United States Patent
Lopez

[11] Patent Number: 5,700,248
[45] Date of Patent: Dec. 23, 1997

[54] MEDICAL VALVE WITH TIRE SEAL

[75] Inventor: George A. Lopez, Laguna Beach, Calif.

[73] Assignee: ICU Medical, Inc., San Clemente, Calif.

[21] Appl. No.: 573,964

[22] Filed: Dec. 15, 1995

[51] Int. Cl.$^6$ .............................. A61M 5/00; A61M 5/14
[52] U.S. Cl. .............................................. 604/249; 604/256
[58] Field of Search .................................. 604/246, 247, 604/249, 256, 283

[56] References Cited

U.S. PATENT DOCUMENTS

| | | | |
|---|---|---|---|
| 3,502,097 | 3/1970 | Müller | 604/249 |
| 4,080,965 | 3/1978 | Phillips | 128/214 D |
| 4,934,655 | 6/1990 | Blenkush et al. | 251/149.1 |
| 5,509,912 | 4/1996 | Vaillancourt et al. | 604/283 |

FOREIGN PATENT DOCUMENTS

WO 93/11828  6/1993  WIPO .......................... A61M 39/00

Primary Examiner—Corrine M. McDermott
Assistant Examiner—Deborah Blyveis
Attorney, Agent, or Firm—Knobbe, Martens, Olson & Bear, LLP

[57] ABSTRACT

A medical valve has a body which includes a wall structure defining an internal cavity having a proximal end and a distal end. The proximal end has an opening sufficiently large to receive a tip of a delivery end of a medical implement which transfers fluid through the delivery end. The valve also has a spike with a tip contained within the cavity and at least one hole located distal the tip. The spike has a passageway in communication with the hole that allows fluid to flow through the spike. The valve also has a resilient seal in the cavity which surrounds the spike. The seal is adapted to be moved into a compressed state upon insertion of the tip of the medical implement into the opening. The seal is sufficiently resilient to return to a decompressed state upon removal of the tip of the medical implement from the opening. In addition, the seal has at least two tires in contact with the spike proximal the hole, preventing the flow of fluid through the valve when the seal is in the decompressed state.

7 Claims, 24 Drawing Sheets

MEDICAL VALVE WITH TIRE SEAL

BACKGROUND OF THE INVENTION

1. Field of the Invention

This invention relates to a closed, patient access system which automatically reseals after administering medication using a standard medical implement that directly connects with the system without the need of any intermediary needles, caps or adaptors. A two-way valve eliminating dead space is used which includes a seal which, upon being compressed by the medical implement, is pierced to open the valve and reseals upon being decompressed, maintaining a fluid tight seal even at high pressures and after repeated uses.

2. Background Discussion

The manipulation of fluids for parenteral administration in hospital and medical settings routinely involves the use of connectors and adaptors for facilitating the movement of fluids between two points. Most fluid connectors and adaptors employ needles to pierce a septum covering sterile tubing or to pierce the septum of a medicament container of fluid. Fluid then passes from the container or fluid fulled tubing into a syringe or second set of tubing. These connectors and adaptors often have mechanical or moving parts. Since the ready passage of fluids through the connectors and adaptors is often critical to patient survival, it is imperative that the connectors and adaptors function reliably and repeatedly. Adaptors and connectors that malfunction during use may be life-threatening. The more mechanical or moving parts such as springs and diaphragms, the more likely that they will function improperly. Improper functioning can result in the introduction of air embolisms into a patient. Thus, the fewer the mechanical parts, the more these connectors can be relied on and the better they will be accepted by the medical community. Many connectors or valves, especially those employing several mechanical components, have a relatively high volume of fluid space within them. This "dead space" within the device prevents the accurate introduction of precise fluid volumes and provides an opportunity for contamination upon disconnection of the device. Connectors and adaptors often include valves that permit or interrupt the flow of fluid along the course of fluid travel. Several of those commonly in use employ metal needles to puncture sterile seals. Such connectors are generally designed to accommodate fluid flow in one direction. This means that the fluid line must have connectors and tube aligned in complementary directions. These connectors often require further manipulation if, for example, the valve is inadvertently assembled in a direction that will not facilitate fluid flow. These manipulations increase handling, thereby increasing both the risk of contamination and the amount of time required to establish the fluid connection.

Metal needles employed as part of connector devices often have through-holes placed at the tip of the needle. Connection of the valve with a flow line involves piercing the needle through a sealed septum. Through-holes placed at the needle tip can core the septum and release free particulates into the flow line. Such an event can prove fatal to a patient. Such through-holes may also become clogged easily with material from the septum. Moreover, the use of a needle with a sharp point may also cause deterioration of the septum.

Reusable connectors and adaptors are preferred for medical applications since components must often be added or removed from a fluid line connected to a patient. Reusable connectors, however, are difficult to keep sterile. Sometimes caps are employed to cover the connector to keep it sterile. Frequently, these caps are lost, or simply not used because they are not readily available when needed.

A closed, patient access system that is easy to use and employs only a valve device in communication with the patient that need not be capped or interconnected with the medical implement through a needle or adaptor, is swabbable, is sufficiently durable to maintain its function after several manipulations, and maintains a fluid-tight seal at high pressures, would be of great benefit to the medical community.

SUMMARY OF THE INVENTION

The valve of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "Detailed Description of the Preferred Embodiments," one will understand how the features of this invention provide its advantages, which include safety, reliable and repeatable performance, simplicity of manufacture and use, and provides long life without malfunction.

A preferred embodiment of a seal used in the present invention comprises a series of O-ring elements stacked together and connected to form a unitary structure. The O-ring elements have increasing diameters, with the smallest diameter element being adjacent the proximal end of the cavity. The O-ring element closest to the proximal end of the seal contacts the wall of the spike proximal the through-holes when the seal is in a decompressed state, thereby preventing fluid from leaking from the interior of the spike through the proximal opening in the housing. It is desirable that at least the next immediate O-ring element also be in contact with the spike proximate the through-holes. Such a design prevents fluid from applying enough pressure on the slit to force the slit open while the seal is in the decompressed state. With the preferred embodiment fluid may reside in the spike and between the spike and the seal distal the through-holes without opening the slit in the seal cap. The seal is designed so that if this fluid pushes the seal upwards slightly, lifting the first and second O-ring elements upwards and off the spike, the O-ring elements immediately distal the first and second elements move up and contact the spike so as to ensure that fluid does not flow through the seal cap and out of the valve. Maintaining this contact around the spike avoids having fluid pressure on the slit force the slit open, permitting the valve to leak.

In another feature of the present invention, the housing is provided with fluid escape space, such as a groove or channel, to permit fluid contained between the exterior of the seal and the housing to escape during compression of the seal. In one embodiment, the proximal end of the housing is provided with at least one groove extending from the proximal end of the housing to indentations contained within the housing. During the compression of the seal, fluid between the exterior of the seal and the housing travels in a proximal direction through the grooves and out of the valve through the proximal end of the housing. In another embodiment, a channel is provided in the fluid escape space through the side wall of the housing. As the seal is compressed, fluid between the exterior of the seal and the housing travels through the channel to the exterior of the valve. As discussed in greater detail below, providing a groove or channel to permit fluid between the exterior of the seal and the housing side wall to escape from the valve during compression of the seal, provides several advantages.

BRIEF DESCRIPTION OF THE DRAWING

The preferred embodiments of this invention, illustrating all its features, will now be discussed in detail. These embodiments depict the novel and non-obvious methods and valves of this invention as well as the medical implement indicators and methods of use thereof, as shown in the accompanying drawing, which is for illustrative purposes only. This drawing includes the following Figures, with like numerals indicating like parts.

DETAILED DESCRIPTION OF THE PREFERRED EMBODIMENTS

Figure 4:
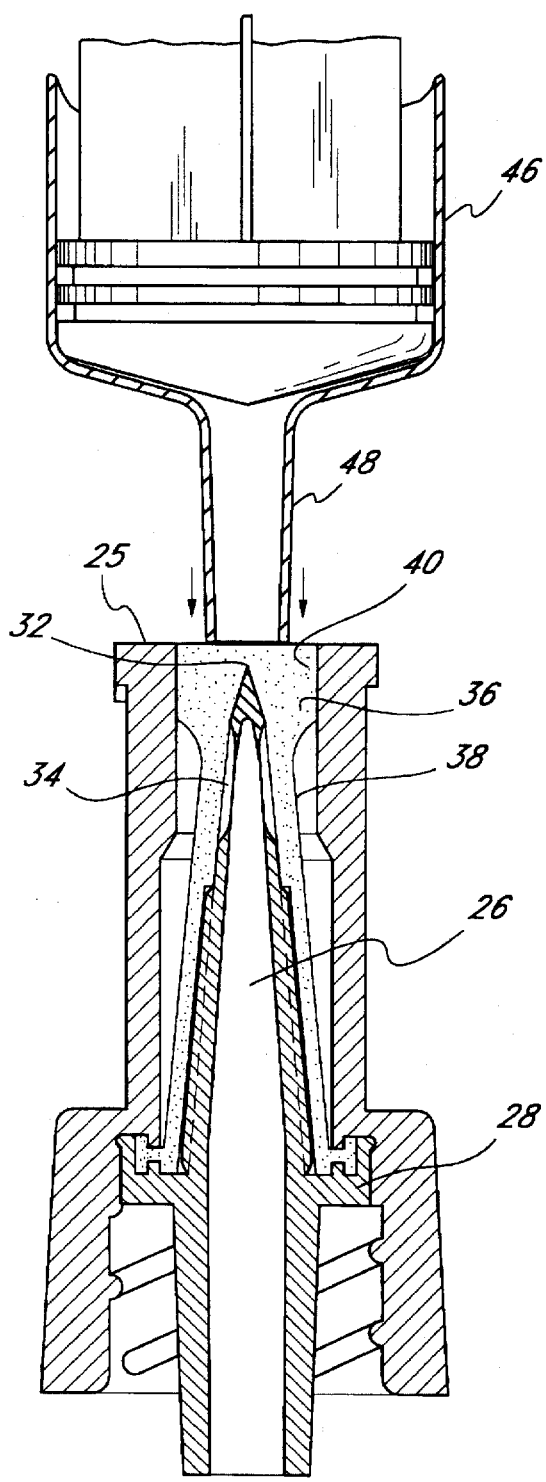
FIG. 4 is a schematic, longitudinal, cross-sectional view of the assembled valve of FIG. 1 before compressing the seal.
Figure 5:
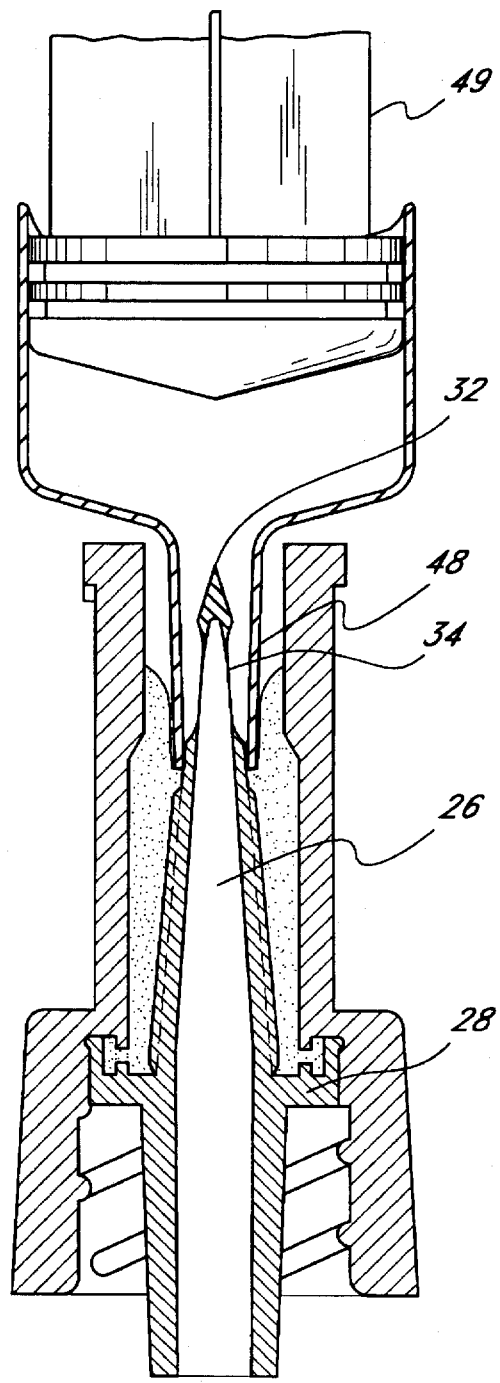
FIG. 5 is a schematic, longitudinal, cross-sectional view similar to FIG. 4 showing the valve during compression of the seal.
Figure 6:
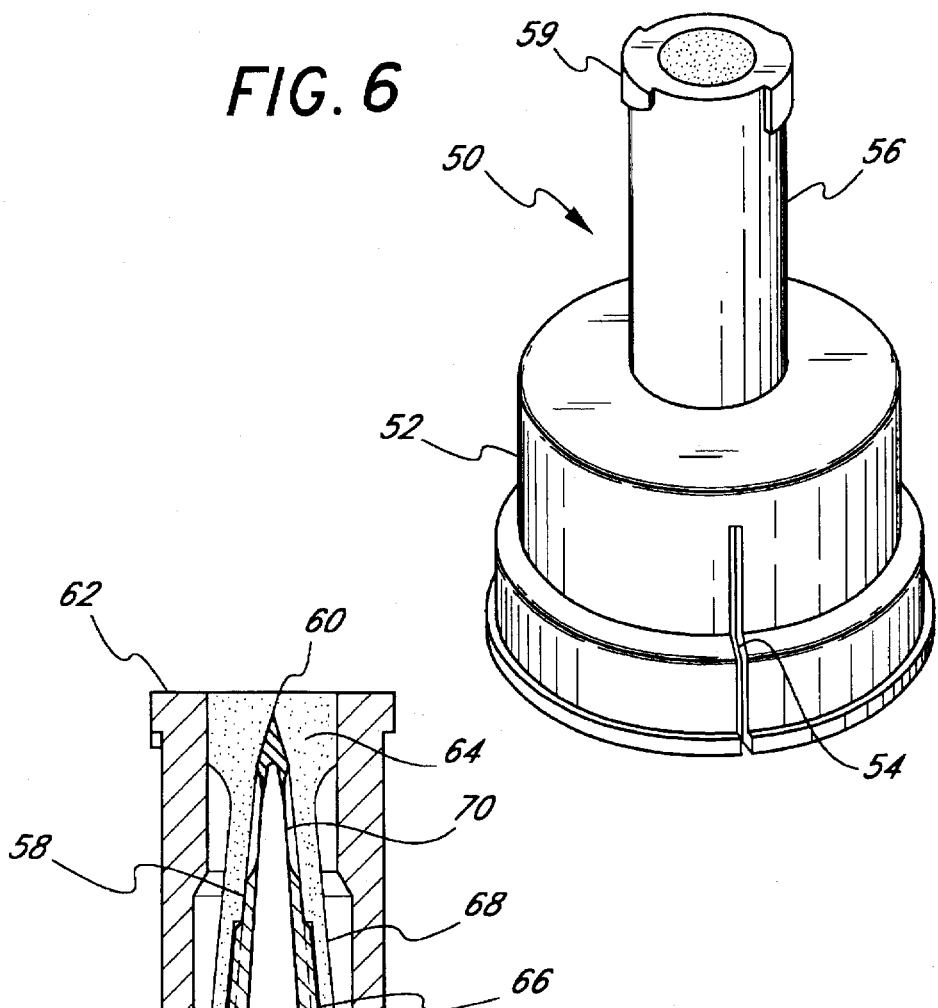
FIG. 6 is a perspective view of a second embodiment of a valve useful in connection with the present invention.

The term "proximal" is used to denote the end of the valve and other components at or near the spike tip 32 in FIGS. 2 through 5, 10 through 12, 14, 16, 24, 25 and 27, and at or near the spike tip 60 in FIG. 6, and at or near the seal cap 92 in FIGS. 8, 9, 13 through 19, 23, 24, 25 and 27. The term "distal" is used to denote the opposite end of the valve, or spike tip, or seal. The term "medical implement" is used to denote any medical tool known to those of skill in the art that can facilitate the passage of fluids, particularly liquids, therethrough. Examples of medical implements that are contemplated include, but are not limited to, tubing, conduit, syringes, IV sets (both peripheral and central lines), piggyback lines, medical valves, and other components. Medical implements are commercially available in standard sizes. Thus, either or both ends of the valve can be provided with fittings to accommodate such standard size medical implements.

The valve is a closed, patient access system which automatically reseals after administering medication using a medical implement that directly connects with the system without the need of any intermediate needles, caps or adaptors. A two-way valve is employed utilizing a reusable seal that may be repeatedly pierced by an enclosed, protected spike rather than an exposed metal needle. The valve facilitates fluid, particularly liquid, transfer while maintaining sterility. The valve is easy to use and is capable of locking in place. After use, the valve is swabbed in the conventional manner with a suitable substance to maintain sterility. The design of the valve avoids accidental needle sticks. As will be discussed in detail below, the valve is useful as a medical connector or adaptor to enable liquid flow from a sealed container.

The first feature of the invention is that the valve has a body including a wall structure defining an internal cavity having a proximal end and a distal end. The cavity has an open space into which the seal is pushed, and preferably has a plurality of radial indentations in the wall structure that are adjacent the seal to accommodate the expansion of the seal upon compression. The proximal end has an opening sufficiently large to receive a delivery end of a medical implement which transfers fluid through the delivery end. In most applications, the delivery end of the implement is tapered inward so that the wall structure and the tapered delivery end fit snug against each other upon insertion of the delivery end into the opening. The proximal end of the cavity preferably is adapted to fit snug with an ANSI (American National Standards Institute, Washington, D.C.) standard end of the medical implement. Typically, the implement is a syringe, a connector or inlet/outlet of an IV set, or any one of a wide variety of conduits used in medical applications.

The second feature is that the spike has a tip with at least one hole located at or near the tip, and a passageway in communication with the hole that allows fluid to flow through this hole. Preferably, the hole is in a side of the spike adjacent the tip and is elongated, having a size of 18 gauge or greater. More than one hole is desirable for many applications, and three, symmetrically located holes inward of the proximal end are preferred. The spike is seated inside the cavity and the tip is embedded in the seal cap located at the proximal end of the seal. The tip of the spike is blunt and rounded so as to avoid deterioration of the seal from repeated penetration by the spike. The spike may include at least one rib which allows air to enter a space between the seal and the spike, thereby facilitating the sealing of the opening when the implement is removed. The spike may have a substantially conical shape, and the seal has a complementarily, substantially conical shaped cavity within it conforming to the shape of the spike.

The third feature is that the resilient seal is adapted to be moved into a compressed state upon insertion of the tip of the medical implement into the opening and returns to a decompressed state upon removal of the tip. The seal in the decompressed state has a section which fills essentially completely a portion of the cavity adjacent the opening. In the compressed state, the seal section is pushed by the delivery end of the medical implement away from the opening and into the cavity. This seal section, known as the seal cap, may have a pre-cut slit in which the proximal end of the spike is embedded. The delivery end of the implement and the seal are adapted to engage so that when the tip of the spike pierces the seal there is essentially no dead space between said delivery end and the seal. Consequently, a predetermined dosage amount of medication is transferred in its entirety to the patient using this invention, with none of the prescribed amount being collected in dead space in the valve. The delivery of an exact amount of medication may be critical in some situations when chemotherapeutic agents are being administered or small children are being treated.

Figures 1, 2:
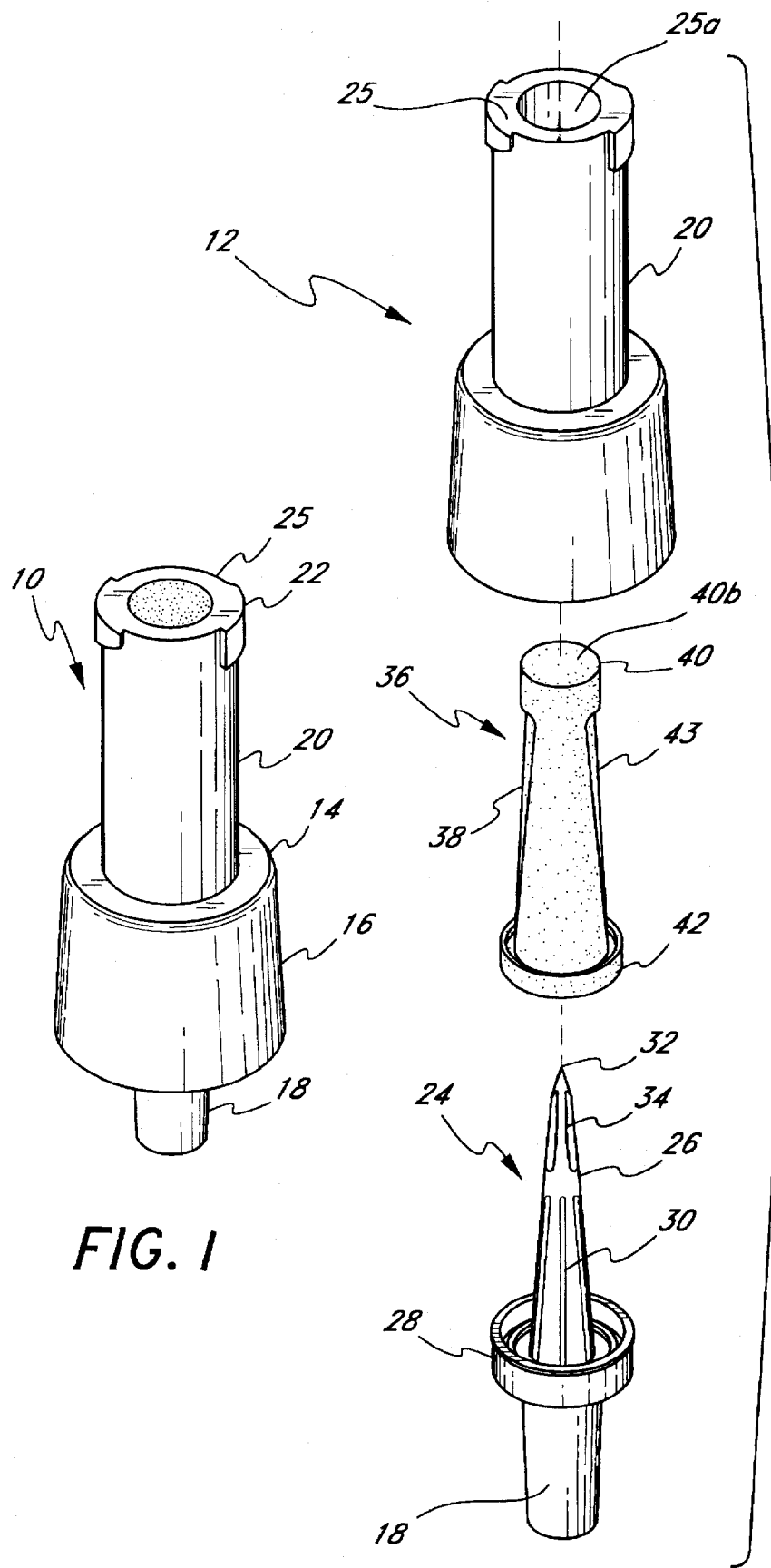
FIG. 1 is a perspective view of the first embodiment of a valve useful in connection with this invention.
FIG. 2 is an exploded perspective view of the valve shown in FIG. 1 illustrating spike, seal, and body or housing components of the invention.
Figure 3:
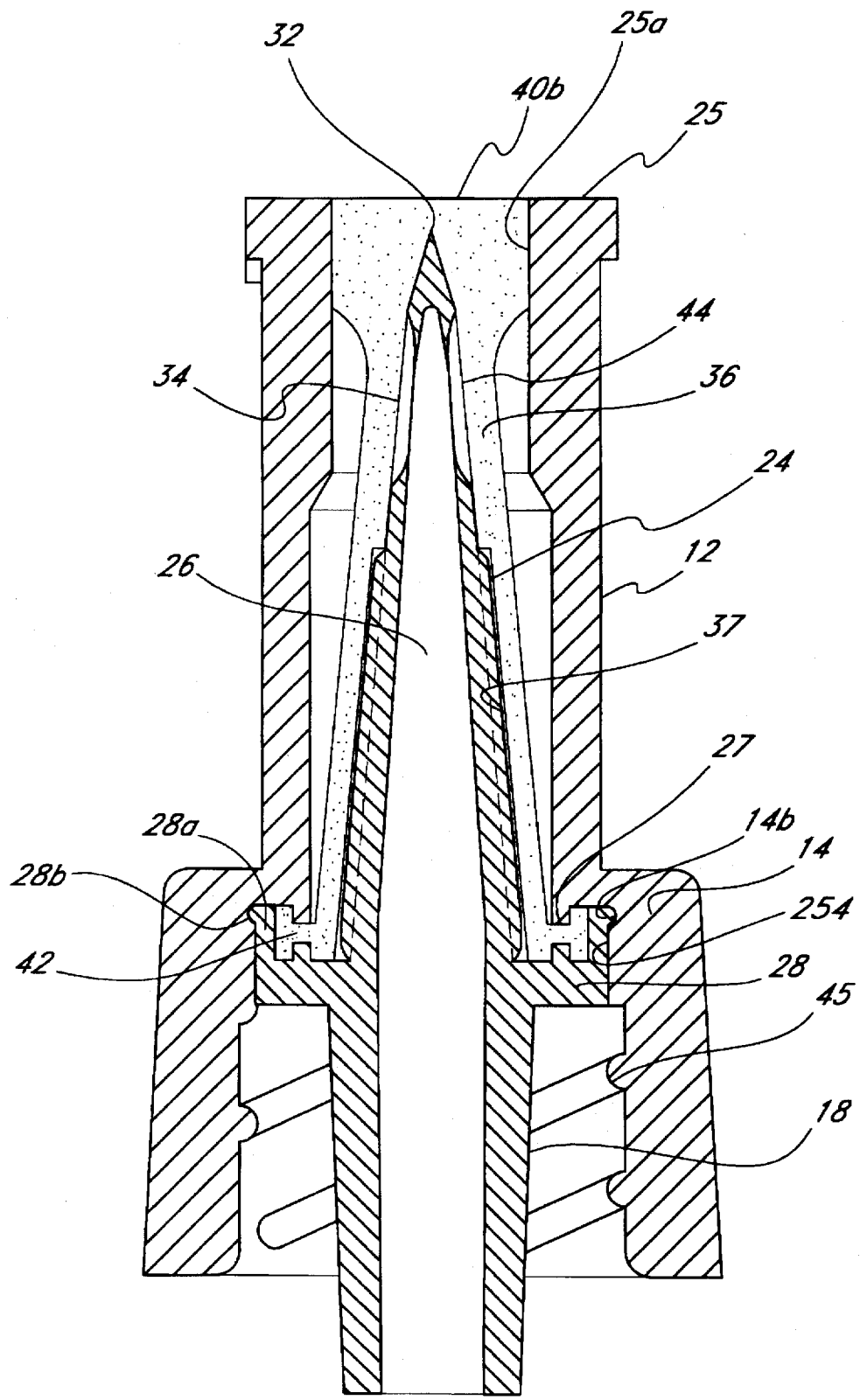
FIG. 3 is a longitudinal cross-sectional view of the assembled valve of FIG. 1.
Figure 13:
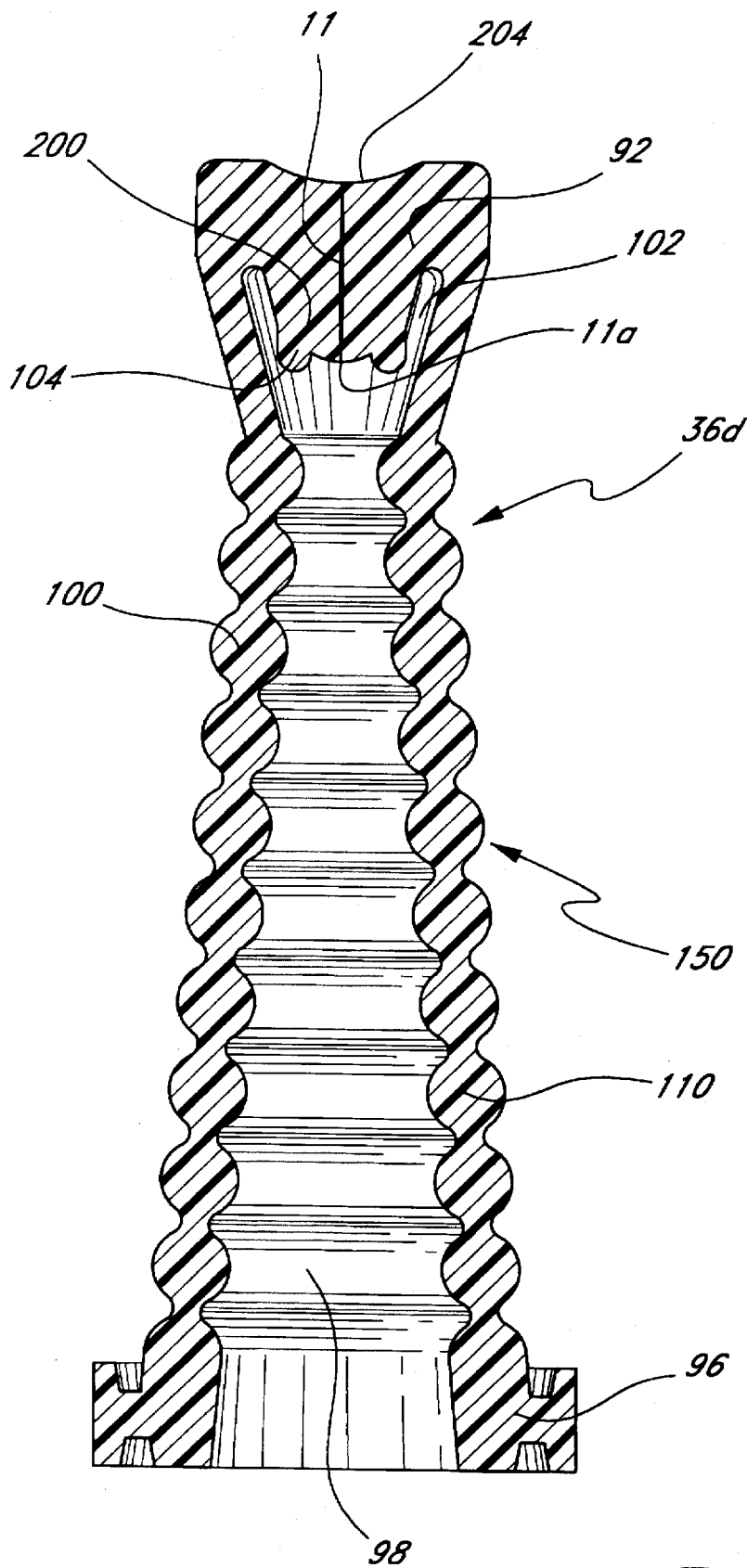
FIG. 13 is a longitudinal cross-sectional view of an additional embodiment of the seal.

As best shown in FIGS. 1 and 2, the first embodiment of valve 10, includes a valve body or housing 12, a spike element 24, and a seal 36. The seal 36 is prepared from a resilient material that is flexible, inert, impermeable to fluid, and readily pierceable by the spike 26. In the valve embodiment shown in FIG. 13 depicting an alternate shaped seal 36d, this seal 36d has a precut slit 11 in its proximal end. This provides a tiny orifice through which the tip 32 of the spike element 24 may easily pass, yet still provides a fluid tight seal upon withdrawal of the spike element. These three components are assembled, as depicted in FIG. 3, with the spike element 24 enclosed to prevent accidental sticks. FIG. 2 illustrates how the housing 12, seal 36, and spike element 24 are attached without the need to use any adhesive or other bonding agent or process. Mechanical connection which provides a fluid tight closure is attained as is discussed subsequently. As shown in FIGS. 4 and 5, the seal 36 moves within the housing 12, being pierced by the spike element 24 to expose the tip 32 of the spike element 24 to allow fluid to flow through the valve 10.

Referring to FIG. 1, one preferred embodiment of the housing 12 has a bell-shaped skirt 16 and an upper, preferably cylindrical, conduit 20. The skirt 16 is integral with, and connected by an annular ring 14, to the upper conduit 20. The skirt 16 creates a shield for an inner conduit 18 of the spike element 24. This inner conduit 18 is preferably cylindrical in shape, and slightly tapered. Inner conduit 18 and upper conduit 20 comprise aligned hollow tubes so that inner conduit 18 and upper conduit 20 are in fluid communication with one another when the spike element 24 pierces the seal 36. There is an annular lip 25 surrounding a circular opening 25a in the top of the conduit 20 (see FIG. 2).

In the first embodiment of the valve, the upper conduit 20 is adapted to receive the tip or nose 48 of an ANSI standard syringe 46 (see FIGS. 4 and 5). It is, however, contemplated that the outer diameter of the upper conduit 20 can be of any size to accommodate the attachment of other connector devices thereto. Advantageously, the proximal end of the upper conduit 20 can be equipped with a locking mechanism to facilitate locking of the valve 10 to a variety of medical implements. For example, referring to FIG. 1, locking ears 22 near the proximal lip 25 of housing 12 are preferably provided such that the housing 12 can be locked into any compatible Luer-Lock device known to those with skill in the art. For example, referring to FIG. 19, conventional Luer-Lock threads 180 can be provided on the outer diameter of upper conduit 20.

Referring to FIG. 2, the spike element 24 has at its distal end the inner conduit 18 and at its proximal end a hollow spike 26 which is integral with the inner conduit. The inner conduit 18 and spike 26 present a continuous passageway for fluid during use. An annular cuff 28 on an intermediate portion of the spike element 24 is integral with, and interconnects, the inner conduit 18 and the spike 26. As illustrated in FIG. 3, the rim 28a of the cuff 28 abuts the underside of the inner ring 14, and has an annular detent 28b that snaps into an annular groove 14b in the underside of the ring. The cuff 28 serves two functions. First, it serves as an attachment device to the underside of the annular ring 14. Second, it serves as a support and attachment device for the seal 36.

The hollow spike 26 has a tapered conical shape, ending in a sharp, pointed tip 32. Preferably, along the length of the spike are raised, protruding ridges 30. These raised ridges 30 extend from the surface of the spike preferably between 0.2–2.0 mm. The ridges 30 are preferably aligned along the length of the spike as illustrated in FIG. 2. These ridges 30 serve to break any vacuum created when the spike 26 is sealed as described hereinbelow. Modifications to the alignment and orientation of the ridges are discussed hereinbelow in association with their function. Distal the spike tip 32, there is situated at least one longitudinal through-hole 34 to permit fluid communication between the inner conduit 18 and the upper conduit 20. Preferably, there are three through-holes 34 within about 10 mm and are preferably within about 5 mm from the spike tip 32. These through-holes 34 may be of any size, however, the larger the size of the through-holes the greater the fluid flow rate through the valve 10. In a preferred valve embodiment, the size of the through-holes 34 are 18-gauge to provide a flow rate three times that of a standard 18-gauge needle.

The seal 36 preferably has a seal cap 40 with a generally flat top surface 40b, an outwardly tapered side wall 38, and a lower lip 42. Its interior is hollow to provide the conically shaped cavity 37 (FIG. 3). Thus, the seal 36 slips easily over the spike element 24 to fit snugly within the cavity 37. The seal lip 42 is seated within the annular cuff 28 and wedged between the cuff and the underside of the ring 14. There are longitudinal grooves 43 (FIG. 2) along the length of the seal 36 which provide air pockets that facilitate compression of the seal 36 during use. The grooves 43 may be of variable shape or size to facilitate seal compression. In the first valve embodiment, there is a single groove 43 which completely surrounds the seal 36 between the seal cap 40 and the lip 42.

The base of the seal 36 has a width such that the seal lip 42 fits snugly into the annular cuff 28. The hollow interior or cavity 37 (FIG. 3) of the seal 36 is preferably tapered to conform internally to the shape of the spike 24, having a wall portion 44 which contacts the spike 24 distal seal cap 40. The exterior of the seal 36 is sized and shaped to fit inside the upper conduit 20 of the housing 12. The cap 40 reseals the valve 10 when the top surface 40b is proximal the through-holes 34. Preferably, the cap 40 substantially fills the opening 25a in the top of the conduit 20. Thus, after assembly, the top surface 40b of the seal cap 40 is essentially flush with the lip 25, so that the lip 25 and seal cap 40 can be swabbed with alcohol or other disinfectant without leakage of disinfectant into the valve 10. It is important that the surface 40b be exposed so that it may be swabbed with a disinfectant.

As best shown in FIG. 3, the spike 24, with contiguous inner conduit 18, is affixed to the housing 12 through the association of the external potion of annular cuff 28 and the internal portion of annular ring 14. Although not necessarily required, these two pieces may be affixed by any one of a variety of methods known to those of skill in the art including, but not limited to, heat sealing, glue, pressure lock, bonding or the like. The seal 36 fits into the annular cuff 28 and is held in place by an internal lip 27 along the internal portion of the annular ring 14 of the housing 12. The length of the spike 24 is such that, after assembly, the tip of the spike rests below the plane defined by the lip 25 of the housing 12. Preferably, the spike tip 32 is approximately from 0.525" to 0.1" below the lip 25 of the housing 12. The seal 36 fits snugly against the spike 24 and is essentially flush with the lip 25 of the housing 12. The spike tip 32 is thus embedded within the seal cap 40 prior to use or may be approximately 0.025" distal the seal cap 40 when the valve 10 is in the closed position. The inner conduit 18 is partially shielded by the bell shaped skirt 16 of the housing 12 (see FIGS. 1–3). The inner surface of the bell shaped skirt 16 preferably has protruding threads 44 as an optional locking mechanism for attaching a medical implement thereto. Further, other medical devices can be pressure fit over the outer portion of inner conduit 18 without direct association with the protruding threads 45.

During use, the valve is designed to be adapted as a two-way valve. The orientation of the valve is independent to fluid flow and dependent on the preferred orientation of the preexisting connections. Thus, the valve can be used as a valve connector for an intravenous central or peripheral piggyback connector in either orientation. Parenteral fluid is delivered to patients through tubing such that the liquid flows from a container through a piercing element into the patient. The containers are frequently changed or additional fluid bottles are added. The valve disclosed herein is designed to interconnect medical implements along the route of fluid delivery to the patient. However, the valve is also useful in any environment in which a resealable fluid valve is desired. During use, a connector of the appropriate size is fitted over the inner conduit 18. Locking can be achieved by a Luer-Lock mechanism, a pressure fit or any other locking mechanisms known to those with skill in the art, as described above. Thus, in one example, fluid passes from the inner conduit 18 into the spike 26. However, fluid flow is locked in place by the seal 36.

FIGS. 4 and 5 illustrate valve activation. In FIG. 4, the medical implement connecting to the proximal end of the valve 10 is a syringe 46. However, this connecting implement could be any number of medical implements known to those of skill in the art. The nose 48 of the syringe 46 is placed on the seal cap 40 inside the lip 25 of the housing 12. The application of pressure on the syringe 46 in the direction of the arrows, as illustrated in FIG. 4 creates pressure on seal cap 40. The resulting downward pressure compresses the seal 36. This pushes the tip 32 of the spike 26 through the seal cap 40 to expose the through-holes 34. Compression is facilitated by the grooves 38. Fluid is now able to flow into the syringe 46, or vice versa, depending on whether fluid is to be withdrawn from the patient or medication injected into the patient. FIG. 5 shows valve 10 opened by insertion of the nose 48 of the syringe 46 into the opening 25a. A syringe plunger 49 in the syringe 46 is retracted thereby creating a vacuum to draw fluid through the valve 10 into the syringe. For intravenous applications, the valve 10 can be orientated in the position diagramed in FIGS. 4 and 5, or it can be rotated 180° such that fluid flows in the opposite direction.

Upon removal of the syringe from the spike 26, as shown in FIG. 4, the seal 36 is free to return to its original shape and cover the through-holes 34. The ability of the seal 36 to return to its original shape is determined by the resiliency of the material used to prepare the seal 36. In addition, the ability of the seal 36 to return to its original shape is facilitated by the protruding ridges 30 formed on the external surface of the spike. During compression, a vacuum may form in the area between the spike 26 and the seal 36, thereby preventing the seal 36 from returning to its original position. The protruding ridges 30 permit air to pass along the spike/seal interface to prevent vacuum formation and allow free return of the seal 36. The ability of the seal 36 to deform reversibly and return to its original position is particularly useful because (1) it immediately stops fluid flow through the valve 10, (2) it covers the recessed spike 26 to maintain its sterility, and (3) it reduces the risk that the spike could inadvertently pierce another object or person. In addition, since the valve 10 lacks movable parts, except for the seal, it is unlikely that when the seal 36 is pushed down, the valve 10 would fail to function. Advantageously, the through-holes 34 are located relatively low on the spike 26. Thus, the through-holes 34 are sealed relatively early in the process as the seal 36 returns to its original configuration when the valve 10 is closed. In one preferred embodiment of the valve, the through-holes 34 are located 0.075" below the spike tip 32 (see FIG. 2). Additionally, the through-holes 34 are sealed even if the seal 36 does not fully return to its original configuration depicted in FIG. 4. Further, the ability of the seal 36 to return reversibly to its original position permits the reuse of the valve 10. Following disconnection, and before reuse, the surface of pierced seal cap 40 is essentially flush with the housing 12. Thus, this flush surface can advantageously be sterilized with alcohol or other surface decontaminating substances. The skirt 16 and upper conduit 20 advantageously shield both connections from the surrounding environment to protect the sterility of the connection. Further, both the skirt 16 and upper conduit 20 function as collection reservoirs to prevent fluid from dripping from the valve 10 during manipulation.

A cover cap (not shown) can be supplied to fit over the upper conduit 20 as further protection for the seal surface between use. Such a cover cap, however, is not needed to maintain sterility since the seal 36 may be swabbed with a disinfectant after each use. The reversibility of the seal 36 makes the valve 10 particularly attractive as a connector valve to provide fluid communication between two fluid lines. Therefore, the valve provides for placing a first fluid line in communication with a second fluid line using the valve disclosed herein. The reversibility of the valve 10 permits multiple fluid lines to be successively added, for example, to a fluid line in direct communication with a patient's vein. Since the valve is easily sterilizable and sealable, fluid lines can be added and removed without disconnecting venous contact.

The valve 10 is preferably prepared from a hard plastic, such as ABS plastic, but it is additionally contemplated that the valve could be prepared from other medically inert materials known to those in the art. The spike element 24 is preferably prepared from the same material as the housing 12. However, a stronger material, such as a poly-carbonate material, may be desirous for the spike element 24 to enable it to pierce a variety of connecting septums and seals. One particular advantage of this valve is that it does not rely on the use of metal needles. This dramatically reduces the risk of skin puncture during use and manufacture. Further, the upper conduit 20 serves as a shield to the spike 26 such that skin contact with the spike 26 is further reduced. The spike 26 need only be strong enough to penetrate the seal cap 40, or if necessary, to pierce a connecting septum.

In the embodiment of the valve illustrated in FIGS. 2–4, the through-holes 34 are placed distal spike tip 32. This placement provides two important advantages. First, the placement of the through-holes 34 facilitates resealing of the valve 10 after use. Second, if the through-holes were placed at the spike tip 32, the holes 34 may core the seal cap 40 thereby introducing seal particulate into the fluid flow and possibly plug the holes 34. Thus, the longitudinal placement of the through-holes distal the spike tip 32 prevents the introduction of particulates into the fluid path and/or plugging of the through-holes 34. It is additionally contemplated that the number and diameter of the through-holes 34 can be adjusted to accommodate different fluid velocities. In a preferred embodiment of the valve, the preferred velocity of fluid passing through the through-holes 34 is equal to or greater than the flow rate through an 18-gauge needle. Through-holes larger than 18 gauge will, of course, facilitate greater fluid flow rates.

An important advantage of the valve 10 is that it has very little dead space, thus the volume of liquid entering into the valve 10 is substantially equivalent to the volume of fluid leaving the valve 10. Further, the total equivalent fluid volume of the valve is very small such that the volume of fluid flowing through the system in order to place the valve 10 in fluid communication with a medical implement such as a syringe 46 is substantially zero.

Figure 7:
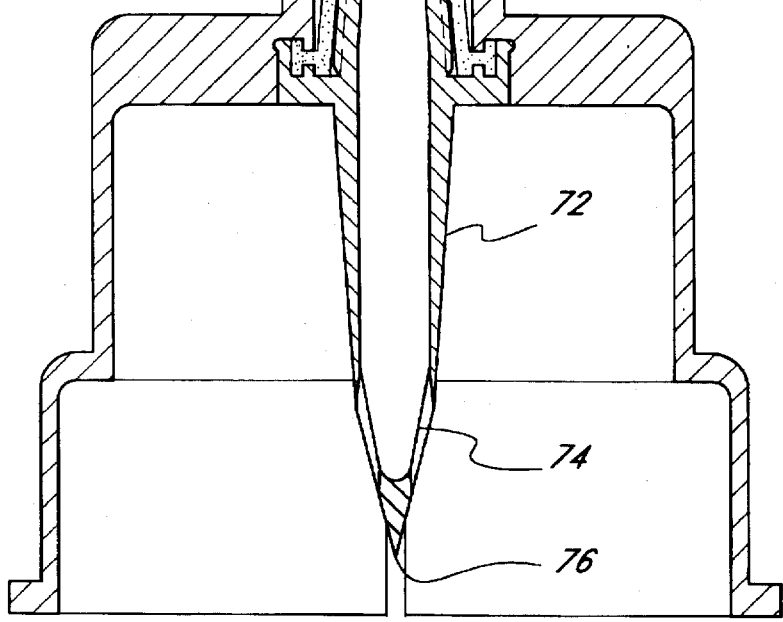
FIG. 7 is a longitudinal cross-sectional view of the valve of FIG. 6.

In another preferred embodiment of the valve, illustrated by FIGS. 6 and 7, a disposable sterile adaptor valve 50 is provided to function as a resealable lid for a container (not shown) of fluid. The fluid can thus be removed from the fluid container or permitted to flow from the container into a medical implement adapted to house fluid in a sterile manner. As is the conventional practice, an open mouth of the container will ordinarily be sealed with a cover member (not shown).

FIG. 6 shows an adaptor valve 50 having a body including an adaptor skirt 52. The adaptor skirt 52 will preferably fit snugly over the open mouth of the container. The skirt 52 may be of any size to accommodate a range of container sizes. A lengthwise slit 54 is preferably provided in at least one location along the length of the skirt to ensure a snug fit between the skirt 52 and the container. A chamber 56, preferably tubular in configuration, extends upward from the skirt 52 and is similar in construction and design to the upper conduit 20 of the first preferred valve embodiment. Similar to the first valve embodiment, the proximal portion of the valve may contain a locking mechanism 59 that preferably comprises a Luer-Lock device or other locking device known to those of skill in the art.

As depicted in FIG. 7, a spike 58 extends upward through a tubular chamber 56. A spike tip 60 is preferably recessed from a proximal lip 62 of the tubular chamber 56. In a closed position, this tip 60 is covered by a seal 64, which is essentially the same as seal 36. Protruding ridges 66 and seal grooves 68 facilitate seal compression and promote closure following use. Thus, in the closed position as illustrated in FIG. 7, the seal 64 covers the through-holes 70 to prevent fluid out-flow from the container. The adaptor valve 50 contains a second spike 72 which points in the opposite direction as the spike 58. These spikes 52 and 72 are in fluid communication with each other. The spike 72 extends downward inside the adapter skirt 52. The two spikes preferably form one component of the valve 50 while the skirt 52 and upper chamber form a second component. These two components can be assembled in a manner like that of the valve 10. The spike 72, like the spike 58, has longitudinal through-holes 74 and a tip 76. The through-holes 74 are located inward of the tip 76. The adaptor valve 50 is thus useable with containers holding sterile medicament having a cover or septum seal at the open mouth of the container. Examples of containers with such seals contemplated for use with this valve include dosage bottles for intramuscular injector antibiotic containers or the like. However, it is also contemplated that the valve 50 can be adapted with its own seal and locking mechanism to permit the valve to be employed on a variety of containers for medicaments or other fluids. Medicaments in these types of containers are preferably maintained under sterile conditions and the volume and nature of the medicament is such that multiple aliquots are intermittently removed over time. If the medicament is reconstituted, then, during use, any covering over the opening on the container is removed to reveal the rubber septum. The adaptor valve 50 is placed over the septum and direct pressure is applied to pierce distal spike 72 through the septum and into the container. A syringe or the like can then be applied, as depicted in FIG. 4, in association with the first preferred valve embodiment, to withdraw fluid from the container. The pressure of the nose 48 over the spike 58 pushes the spike tip 60 through the seal 64. At the same time, the seal 64 is compressed. Compression is accommodated by the seal grooves 68. Fluid is withdrawn from the container and the syringe is removed from the spike 58. Release of the pressure applied to the seal 64 permits the seal 64 to return to its original configuration. The spike ridges 66 facilitate movement of the seal 64.

Often the ingredients housed in containers are those that can be lyophilized at purchase. Lyophilized ingredients require reconstitution before use. If the medicament requires reconstitution before use, then sterile water, saline, or other fluid can be introduced into the container before fluid is extracted. The two-way nature of the valve permits this without any special adaptation. After the syringe is removed, the adaptor valve 50 automatically seals. Subsequently, aliquots can be removed from the container by syringe or the like. Alcohol or other compatible surface sterilizing agents can be used to wipe the lip 62 and seal 64 before each use. Similar to the first valve embodiment, it is additionally contemplated that a cap can be provided to fit over the upper chamber lip 62 between uses.

The adaptor valve 50 can be adapted to function as a medicament adaptor for an intravenous container. In this case, the adaptor valve 50 is placed on a medicament container for intravenous delivery and attached via tubing to an intravenous feed. Thus, the adaptor valve 50 can be placed in fluid communication with a connector valve of FIG. 1 to facilitate the flow of medicament from intravenous drip bottles.

Figure 9:
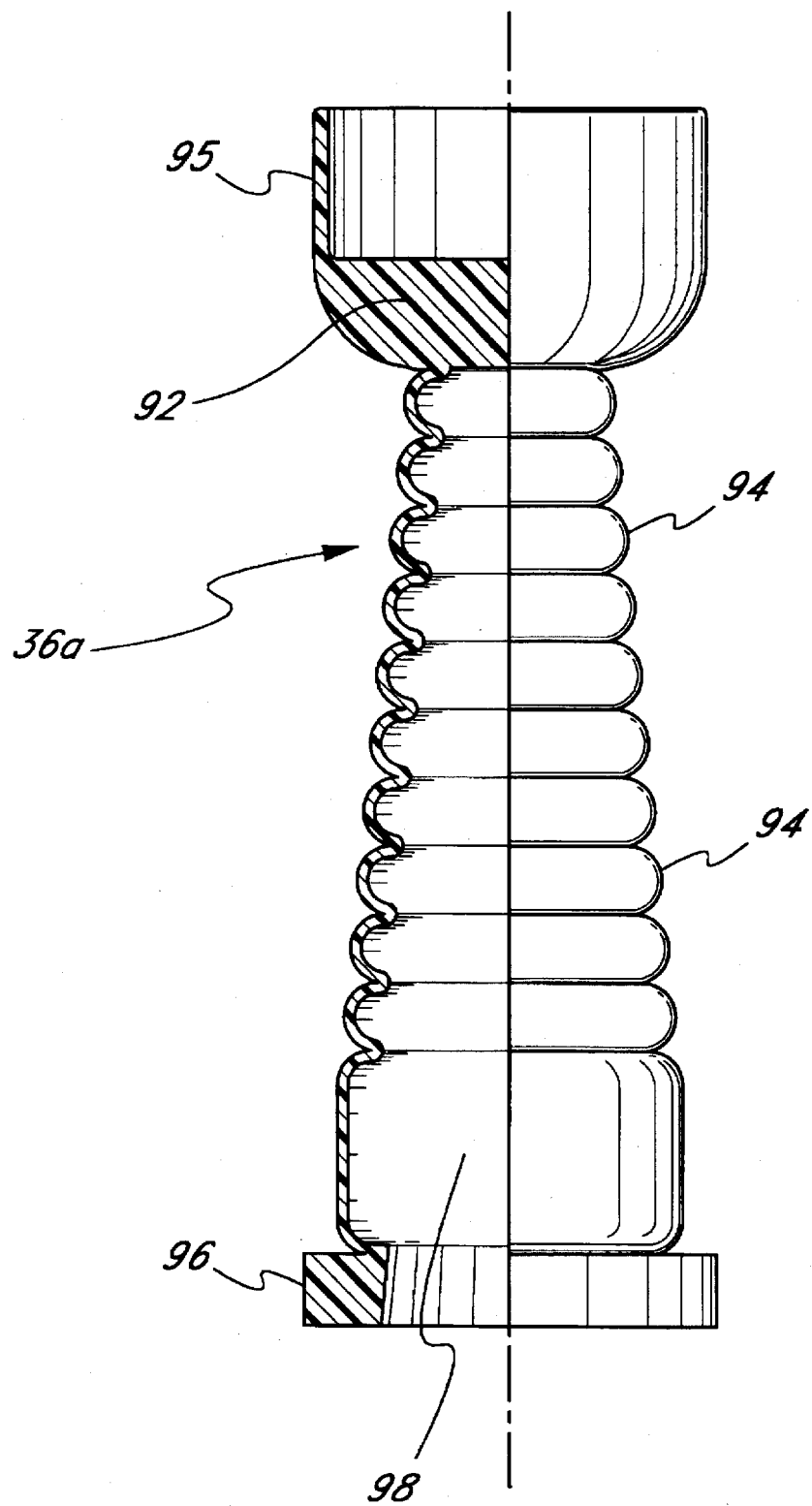
FIG. 9 is a side elevation view, partially in cross-section, of an embodiment of the seal.

An alternative embodiment of the seal, a seal 36a, is shown in FIG. 9. The seal 36a comprises a seal cap 92 at the proximal end thereof and a seal lip 96 at the distal end thereof. A cup-like annular flange 95 is provided proximal the seal cap 92. The seal cap 92 and seal lip 96 are connected by a seal wall consisting of a plurality of ringed wall portions 94 that expand and collapse in an accordion like fashion. During compression of the seal 36a, the diameter of the ringed wall portions 94 expand outward in the radial direction. There are air pockets 13a (FIG. 10) between ring portions 94 and the housing and air pockets 13b between the spike 24 and seal 36a. The seal 36a contains a cavity 98 distal the seal cap 92 and adjacent the ringed wall portions 94. The seal 36a interacts with the spike 26 (FIG. 2) and other components of the valve in a similar fashion to the seal 36 of FIG. 2.

Figure 10:
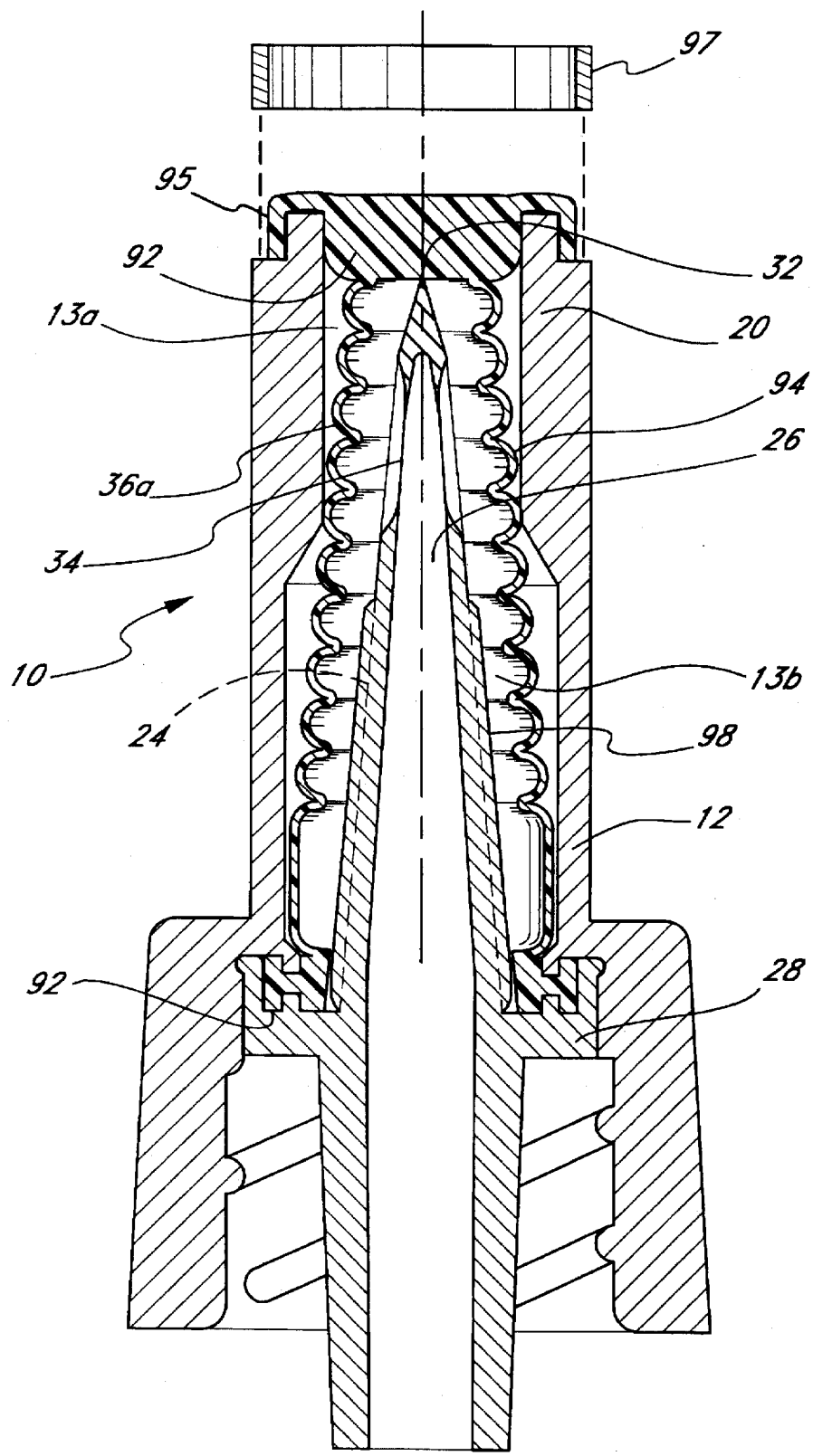
FIG. 10 is a longitudinal cross-sectional view of the assembled valve of FIG. 1 using the seal of FIG. 9.

Referring to FIG. 10, the cup-like annular flange 95 can be stretched around the upper conduit 20 and held in place by an annular ring 97. This creates a trampoline-like effect that assists returning the seal 36a to a decompressed state after withdrawal of a syringe (not shown). This embodiment has two advantages. First, the proximal end of the valve 10 can be swabbed with alcohol or other disinfectant without leakage of disinfectant into the valve 10. Second, by affixing the cup-like annular flange 95 to the upper conduit 20 at the proximal end thereof with the annular ring 97, the repeated deformation and reformation of the seal 36a is assisted.

Figure 11:
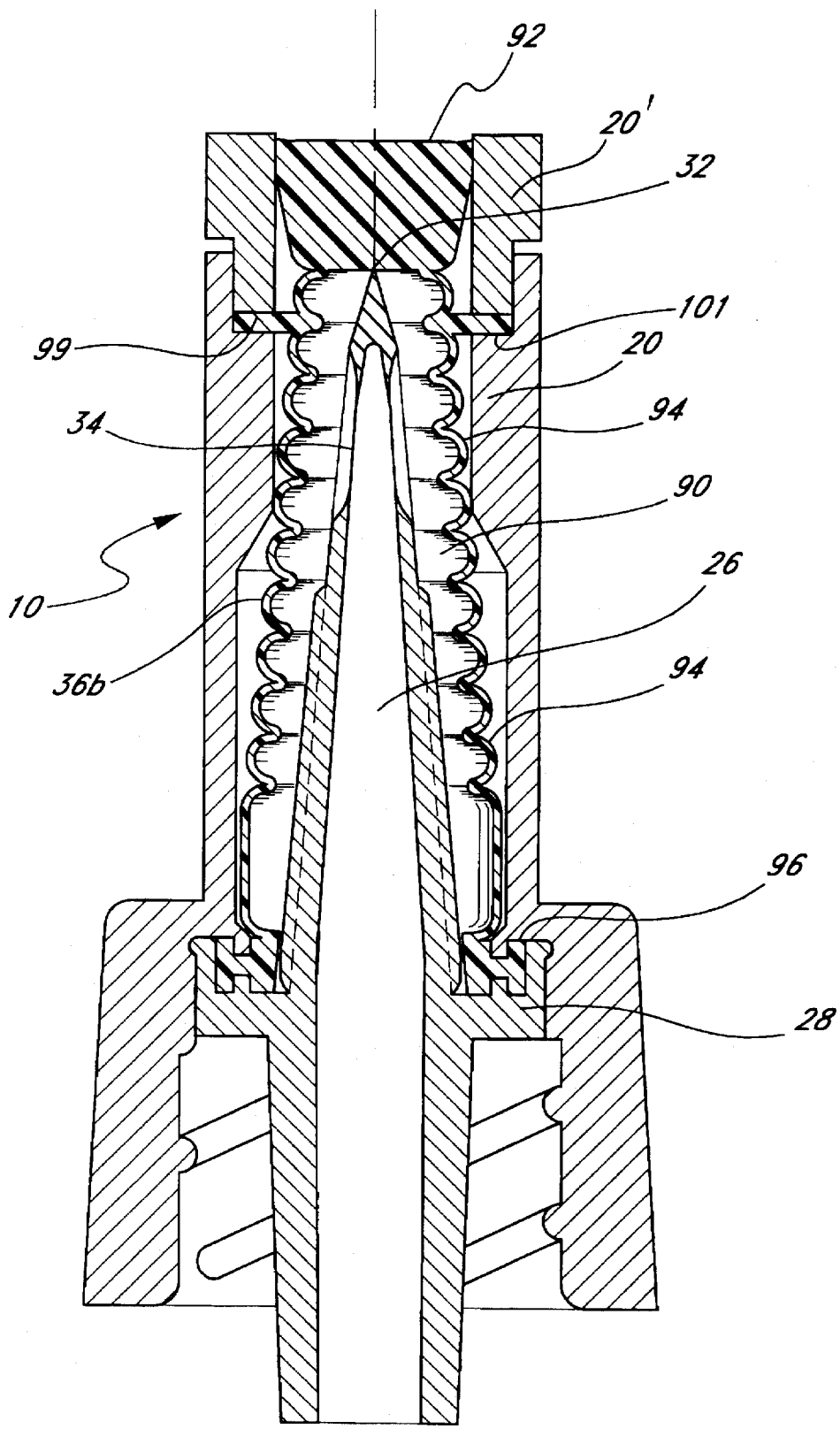
FIG. 11 is a longitudinal cross-sectional view of the assembled valve of FIG. 1 using another embodiment of the seal.

In an alternative embodiment of the seal, the seal 36b is shown in connection with the valve 10 in FIG. 11. The seal 36b is similar to the seal 36a shown in FIGS. 9 and 10, as the seal 36a is comprised of a seal cap 92, a side wall consisting of ringed wall portions 94 and a seal lip 96. The seal 36a also has an outwardly extending ring 99 which is at a right angle with respect to the longitudinal axis of the valve 10. This ring 99 is used to attach the seal 36b to the upper conduit 20. Preferably, an upper conduit annular plug 20' is inserted within the upper conduit 20 to create a tight fit between the perpendicular ring 99, a ledge 101 in the upper conduit 20, and the plug 20'. The ring 99 assists in the reformation of the seal 36b to enclose the spike 26 upon withdrawal of a syringe (not shown).

Figure 12:
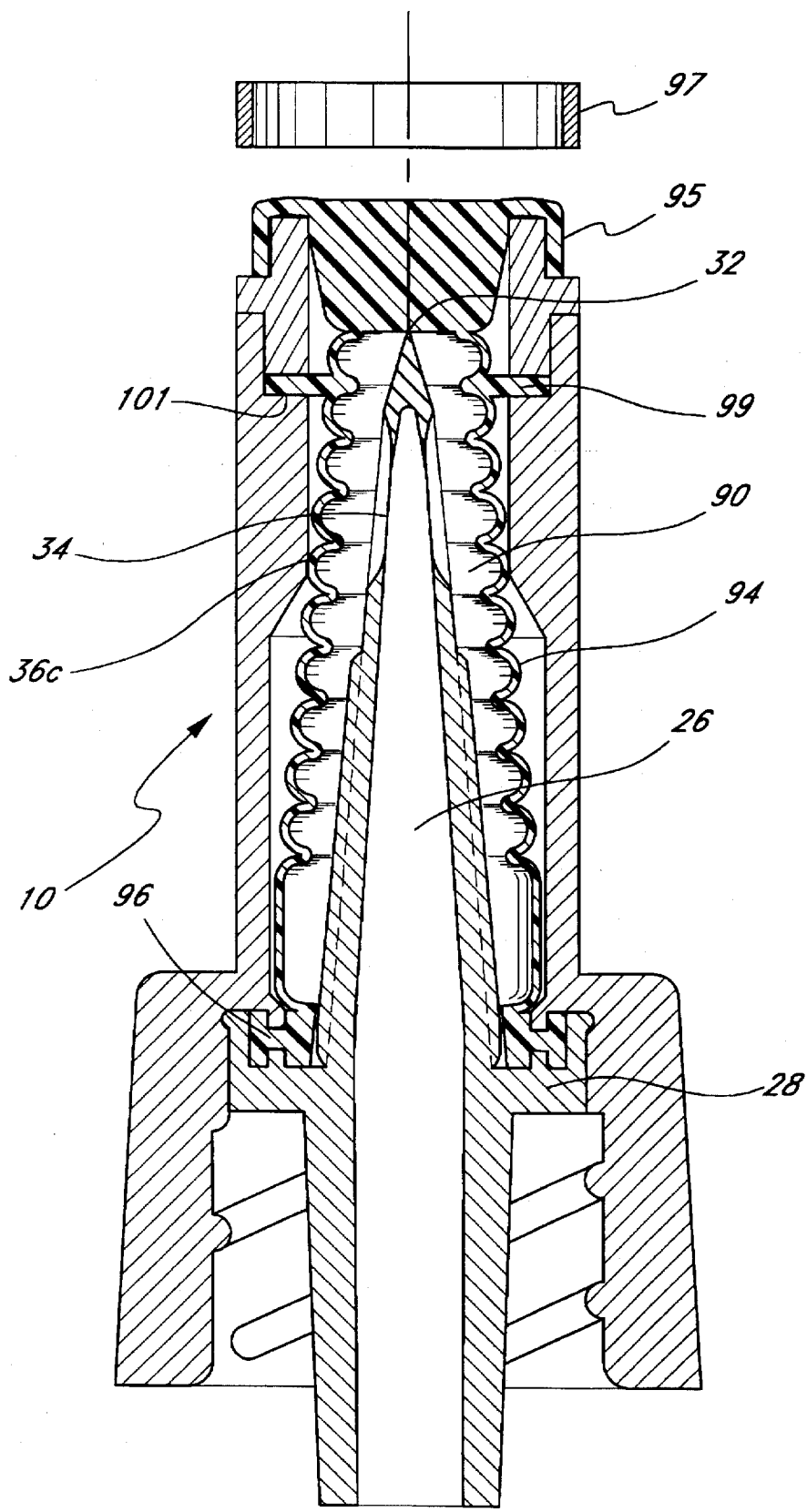
FIG. 12 is a longitudinal cross-sectional view of the assembled valve of FIG. 1 using yet another embodiment of the seal.

As shown in FIG. 12, the cup-like annular flange 95 and ring 99 may both be used in connection with the valve 10, to provide the seal 36c. This seal 36c, provides rapid reformation upon withdrawal of a syringe (not shown) and realizes the advantages of both the seals 36a and 36b.

Another alternative embodiment of the seal, a seal 36d, is shown in FIG. 13. In this embodiment, the seal 36d is comprised of a seal cap 92, a seal lip 96, and a side wall 150 comprised of circular tires 100 stacked in series one on top of an adjacent larger diameter lower tire. The circular tires 100 are preferably solid throughout the diameter of the cross-section thereof. These circular tires 100 will deform and reform upon, respectively, compression and decompression of the seal 36d, thereby exposing or covering a spike (not shown) as the case may be.

Figure 14:
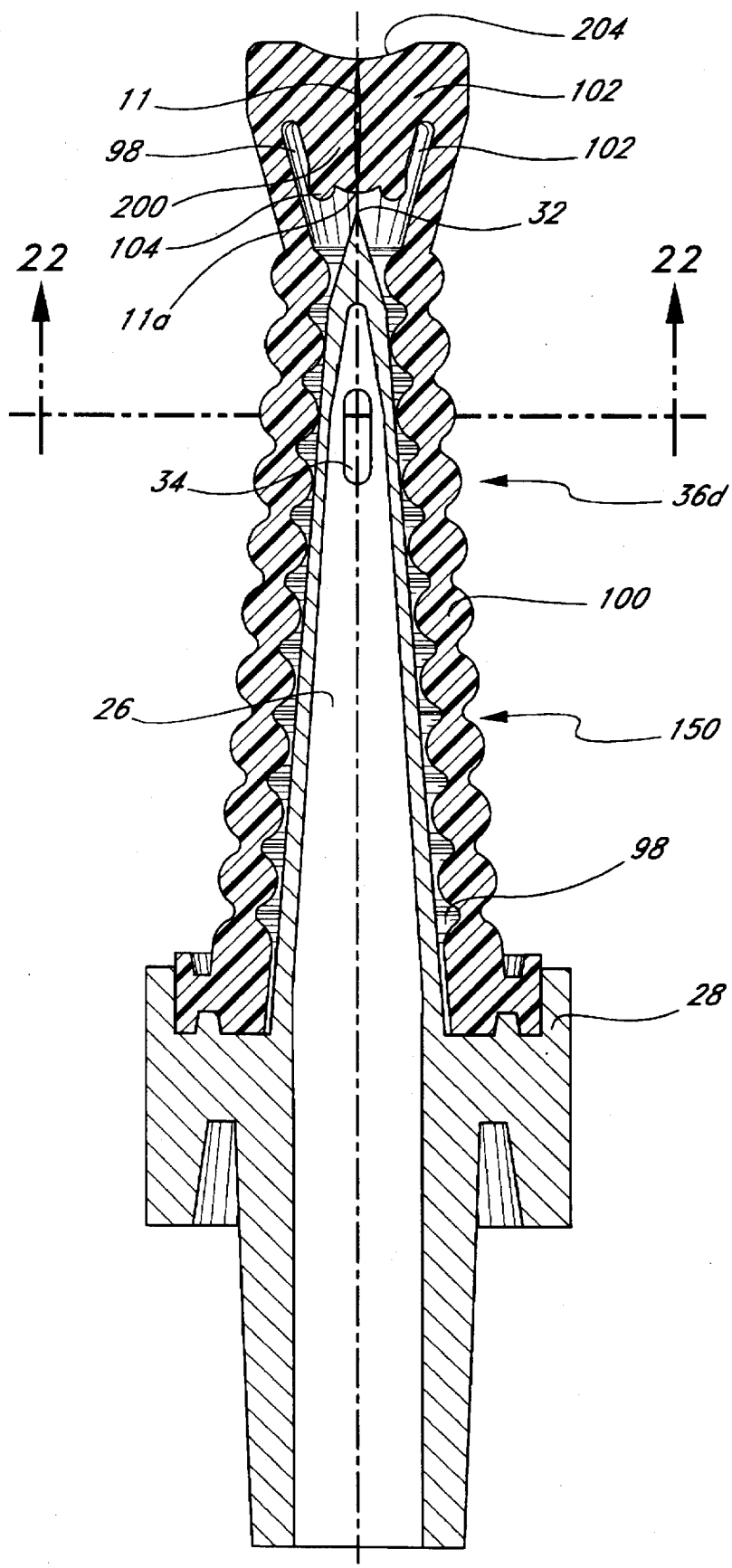
FIG. 14 is a longitudinal section of the seal shown in FIG. 13 used in connection with the spike device shown in FIG. 2.
Figure 15:
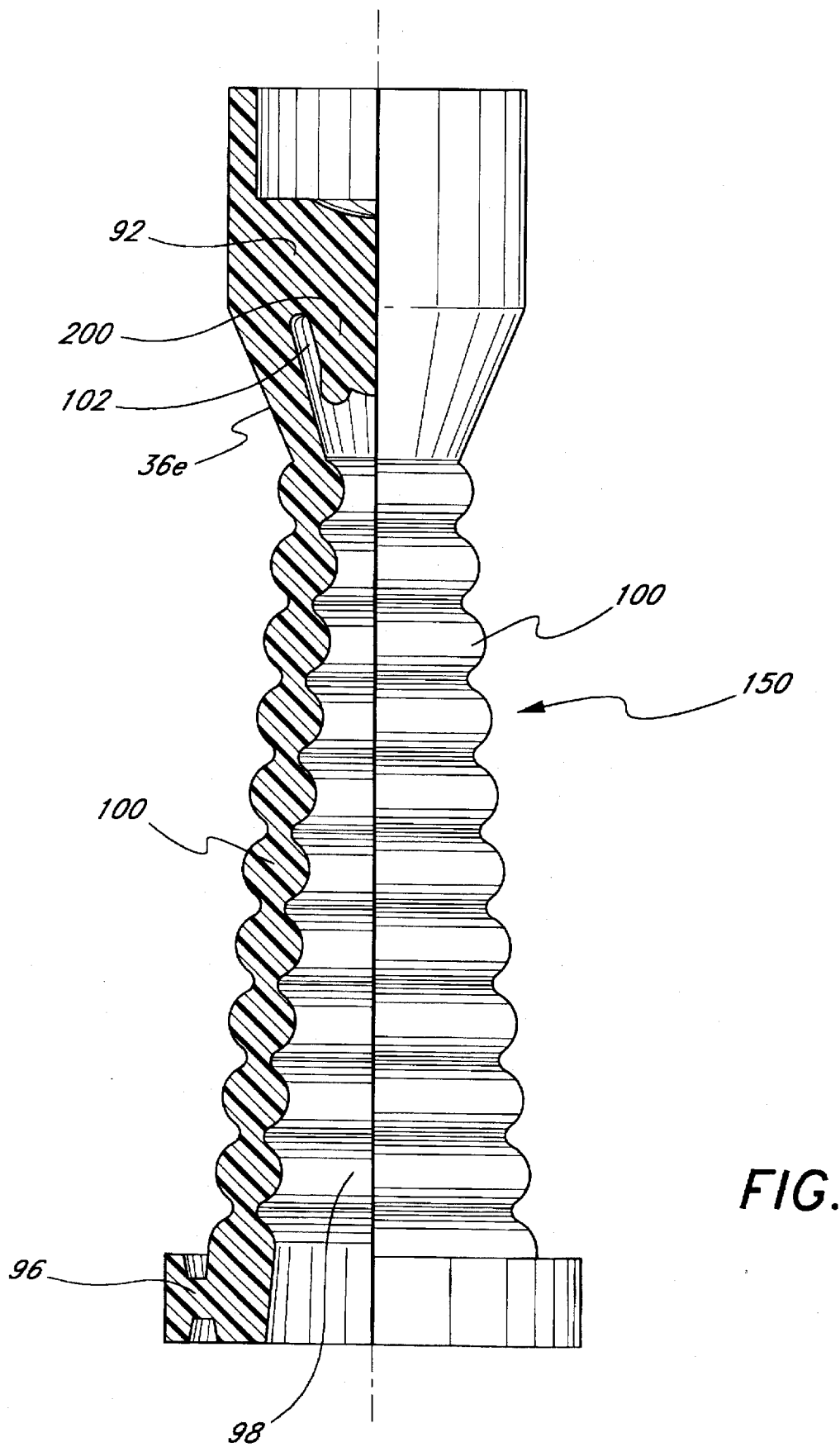
FIG. 15 is a longitudinal partial cross-sectional view of a still further embodiment of the seal of this invention.
Figure 16:
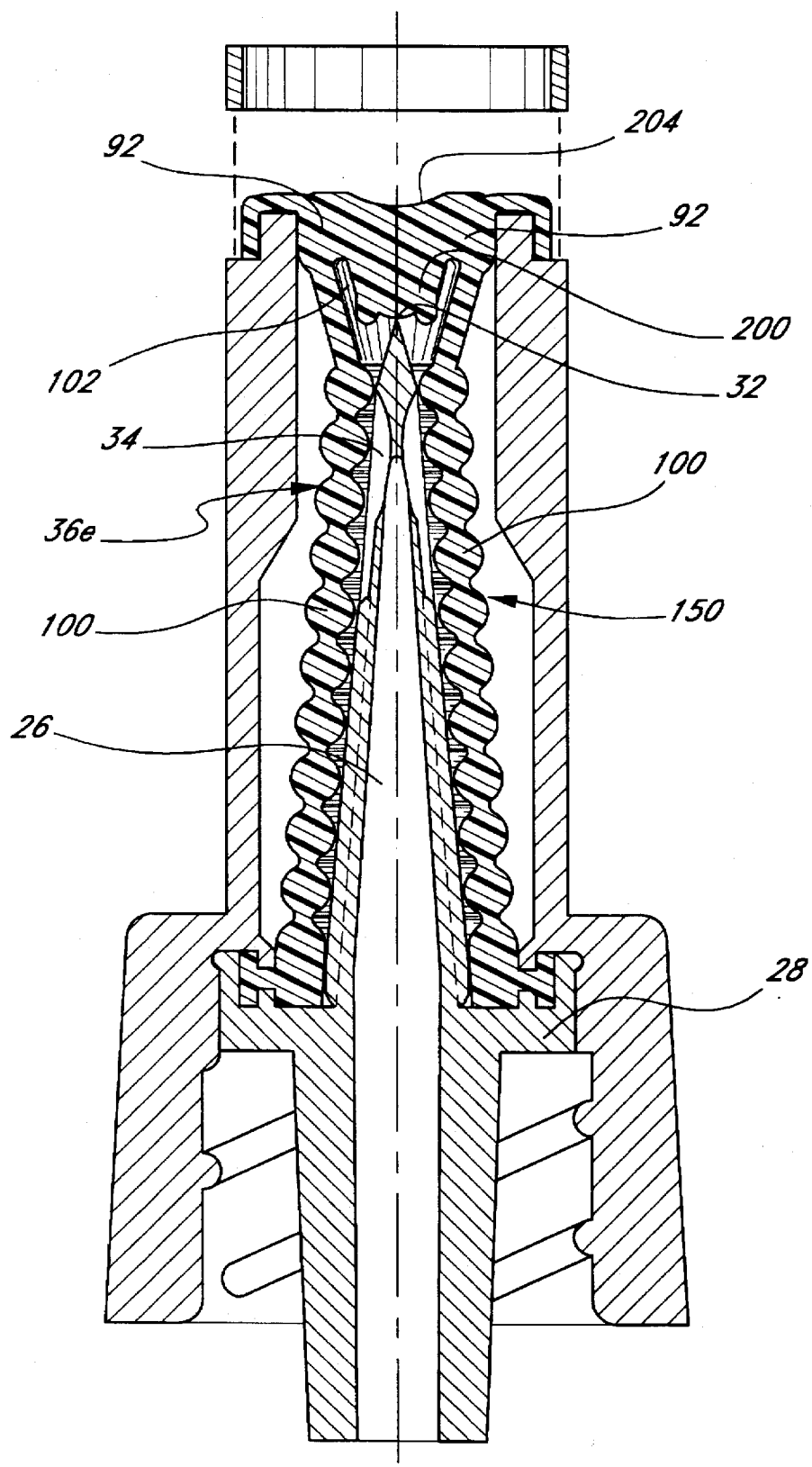
FIG. 16 is a longitudinal cross-sectional view, after assembly, of the valve shown utilizing the seal of FIG. 15.
Figure 17:
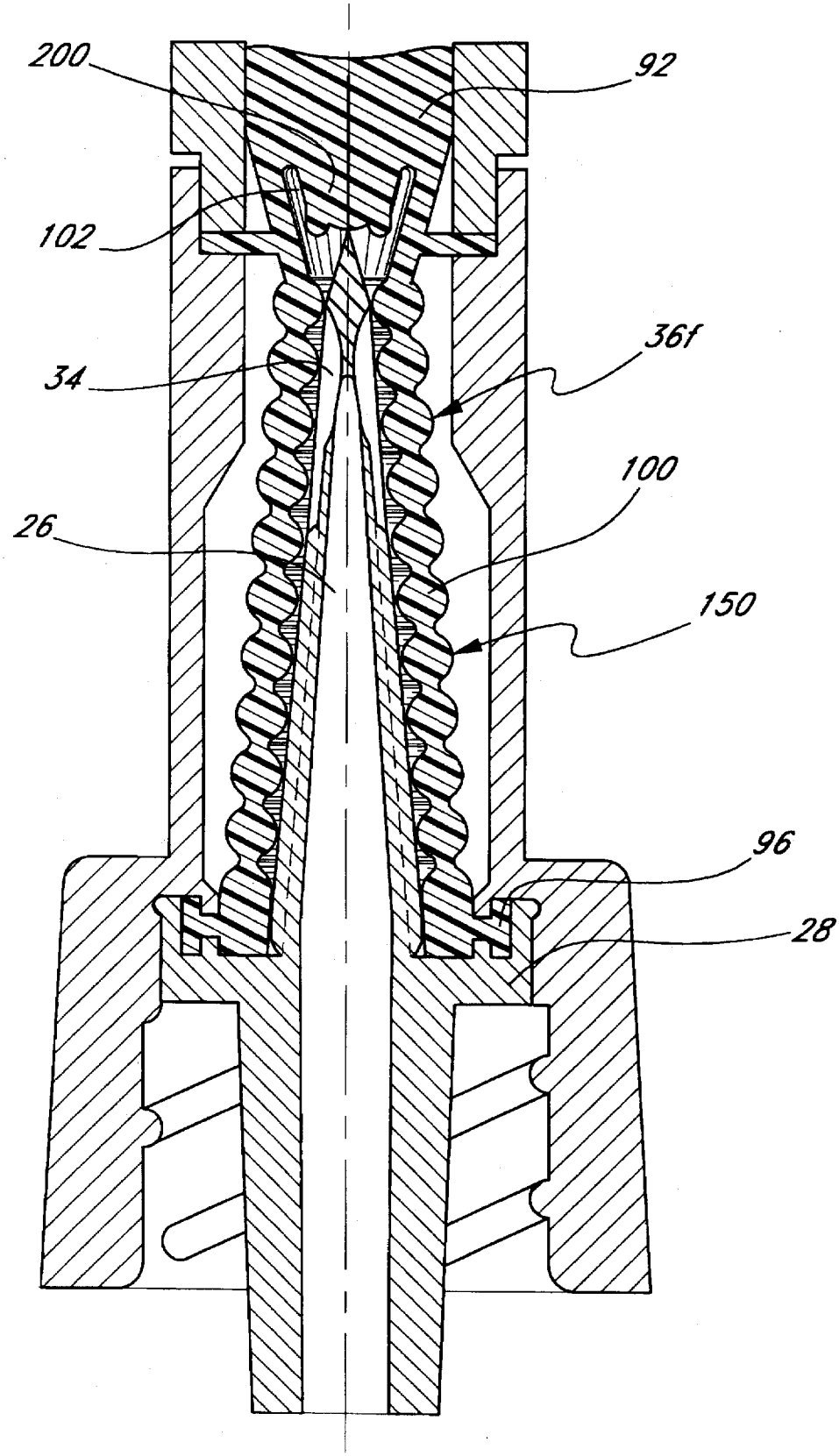
FIG. 17 is a longitudinal cross-sectional view, after assembly, of the valve shown utilizing still another embodiment of the seal.
Figure 18:
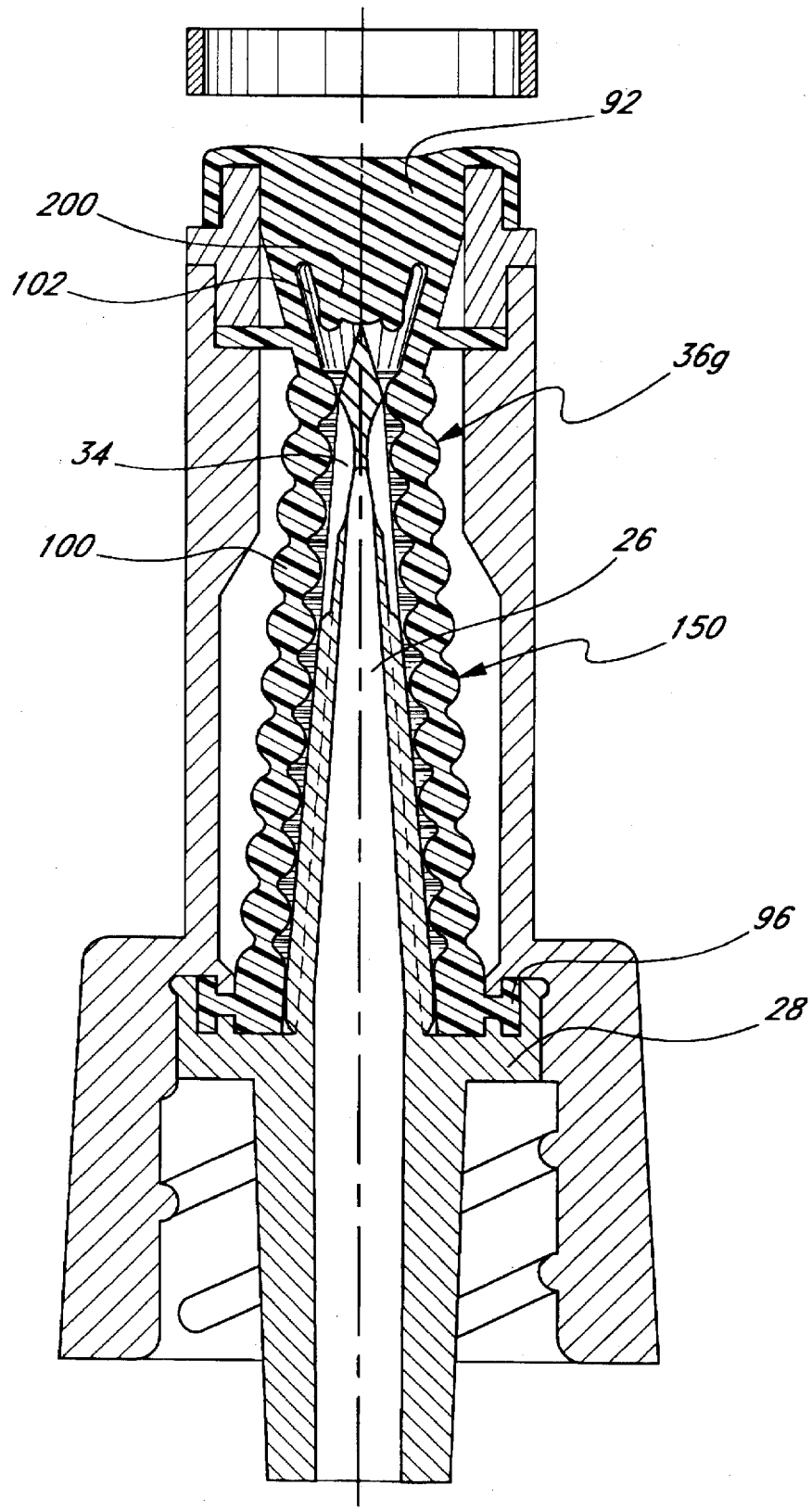
FIG. 18 is a longitudinal cross-sectional view, after assembly, of the valve utilizing yet one more embodiment of the seal.
Figure 19:
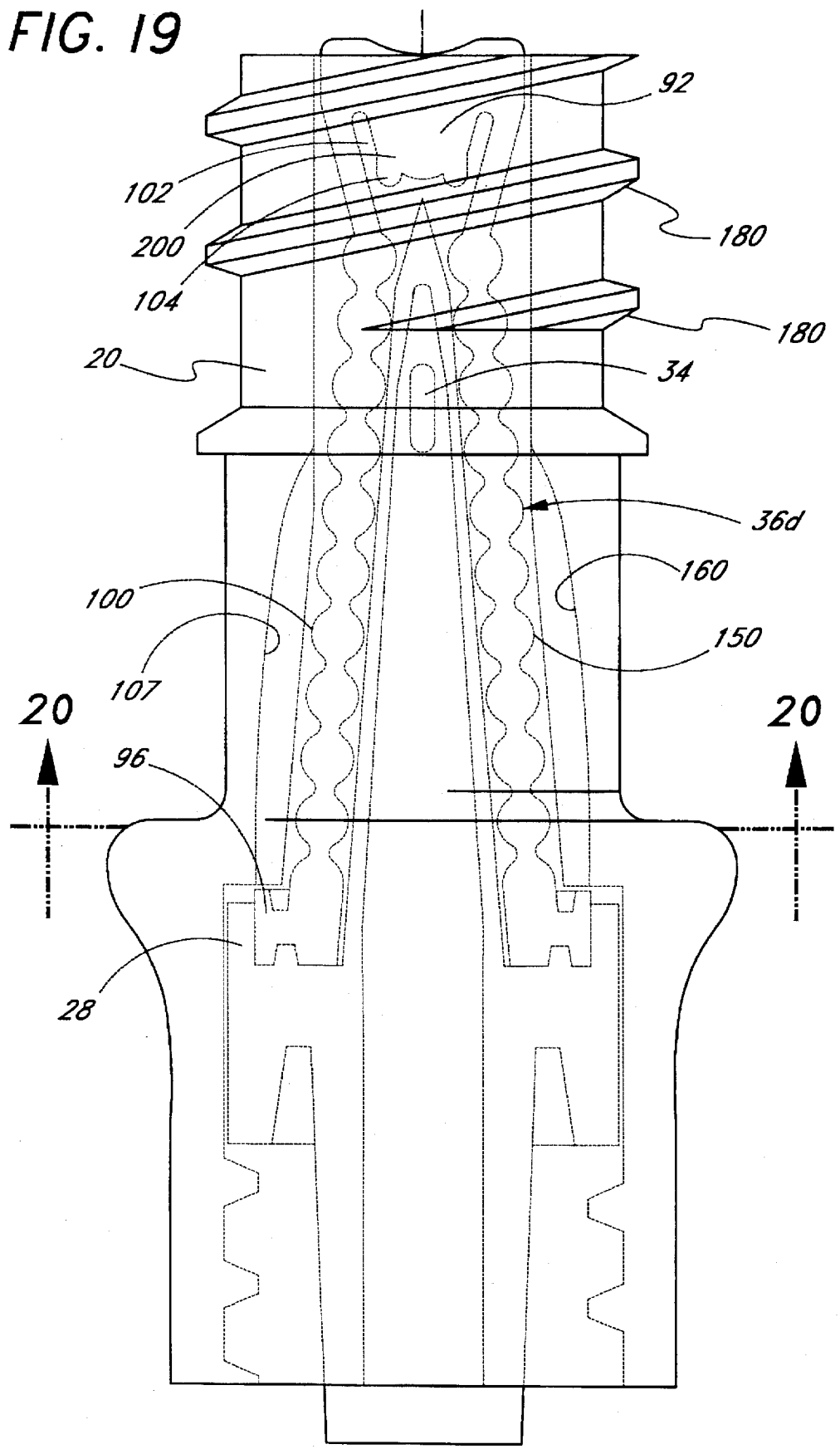
FIG. 19 is a side elevation view, after assembly, of the seal and spike shown in FIG. 14 connected to the body or housing shown in FIGS. 20 and 21.
Figure 20:
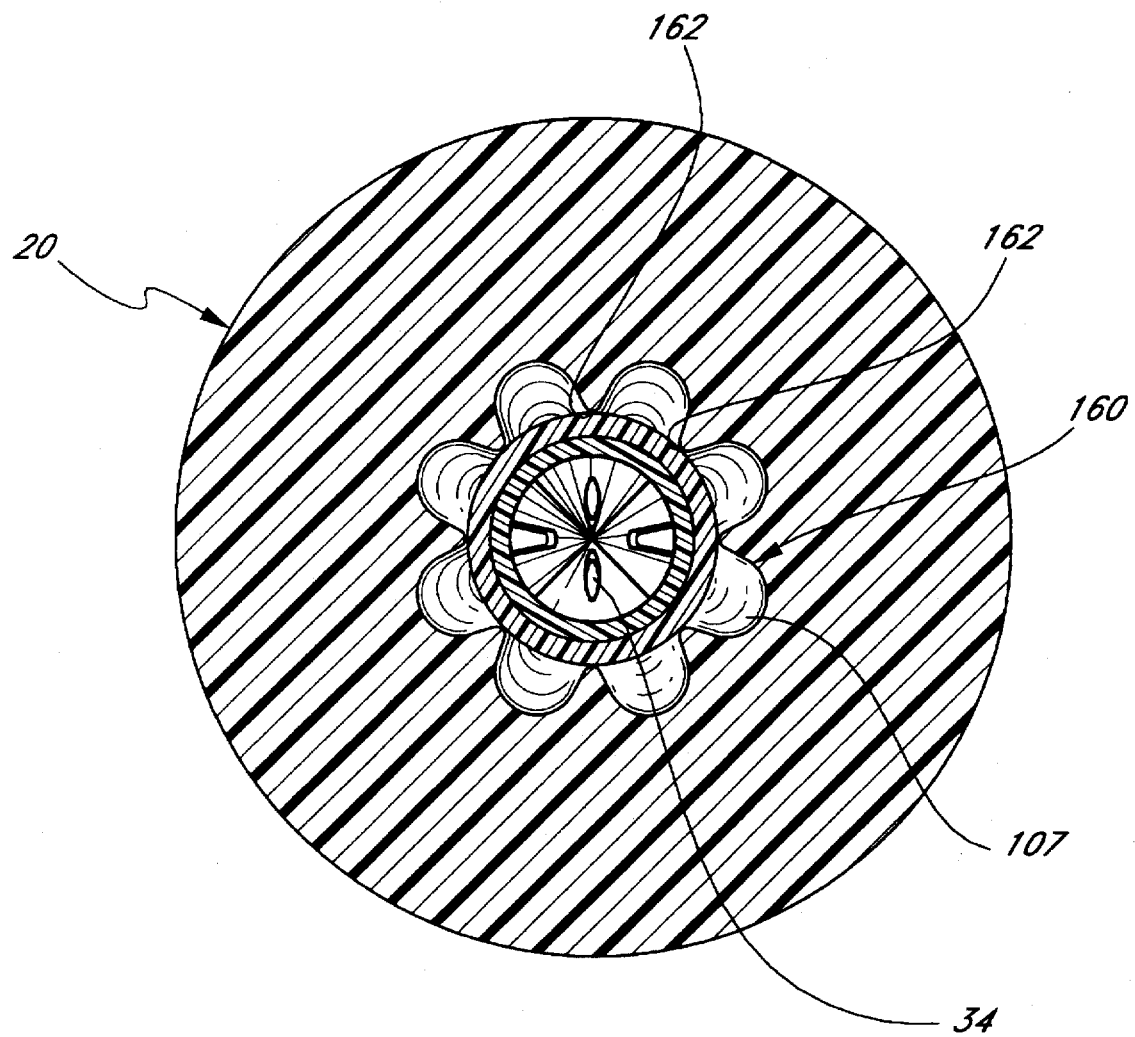
FIG. 20 is a cross-sectional view taken along line 20—20 of FIG. 19.
Figure 21:
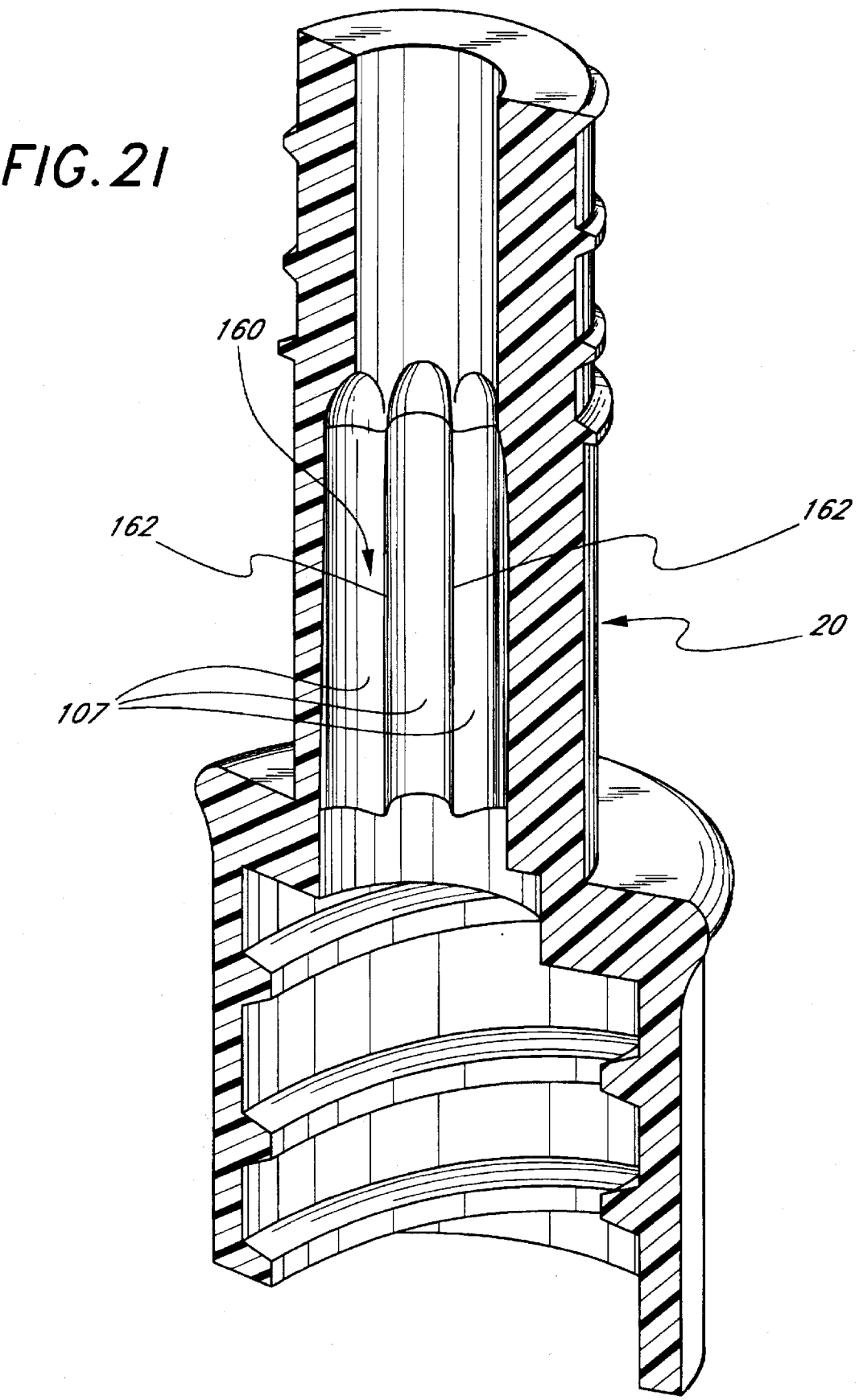
FIG. 21 is a perspective view of the housing shown in FIG. 19, with sections broken away to show the wall structure of the cavity containing the seal shown in FIG. 13 and 14.

As mentioned above, preferably the seal 36d has a precut slit 11 in the cap 92 lying along the longitudinal axis of the valve 10. The seal cap 92 has a unique configuration that insures that the slit 11 closes and is sealed upon withdrawal of a syringe (not shown) and reformation of the seal 36d. It includes an enlarged, internal, pressure responsive member 200 which is integral with the seal cap 92. Between the proximal end of the side wall 150 and the member 200 is an annular space 102 which is filled with the fluid in the cavity 98. This fluid is under pressure, for example at the blood pressure of the patient to which the valve 10 is attached. Referring to FIG. 14, fluid, for example the patient's blood, flows through the holes 34 in the spike 26, filling the cavity 102. This fluid presses against the exterior of the member 200, closing the slit 11 when the seal is decompressed as shown in FIGS. 14 and 19. The pressure from this fluid creates a high pressure seal which prevents fluid from escaping valve 10 through the slit 11. There is a semi-cylindrical annular flange tear ring 104 on the end of the member 200 which advantageously extends the useful life of the seal 36d.

Preferably, there is a tear ring 104 integral with the member 200 along the perimeter of the internal surface the member 200, and a slight saucer-like depression 204 in the external surface of the seal. The pressure responsive element in the decompressed state closes any orifice in the seal 36d to provide an essentially fluid-tight seal while in the decompressed state. The pressure responsive member 200 enables the valve to maintain a fluid-tight seal even at very high pressures sometimes experienced in medical applications, particularly when the valve 10 is connected to a patient's artery. The center of the member 200 and the annular space 102 are coaxial with the entryway 11a to the orifice 11. The pressurized fluid fills the annular space 102 to apply pressure that compresses the member 200 to tightly close the entryway 11a to the orifice 11. In a preferred valve embodiment the distance from the entryway 11a to the proximal end of the seal cap 92 is from 0.500 to 0.075 inches and more preferably approximately 0.100 inch.

Figure 22:
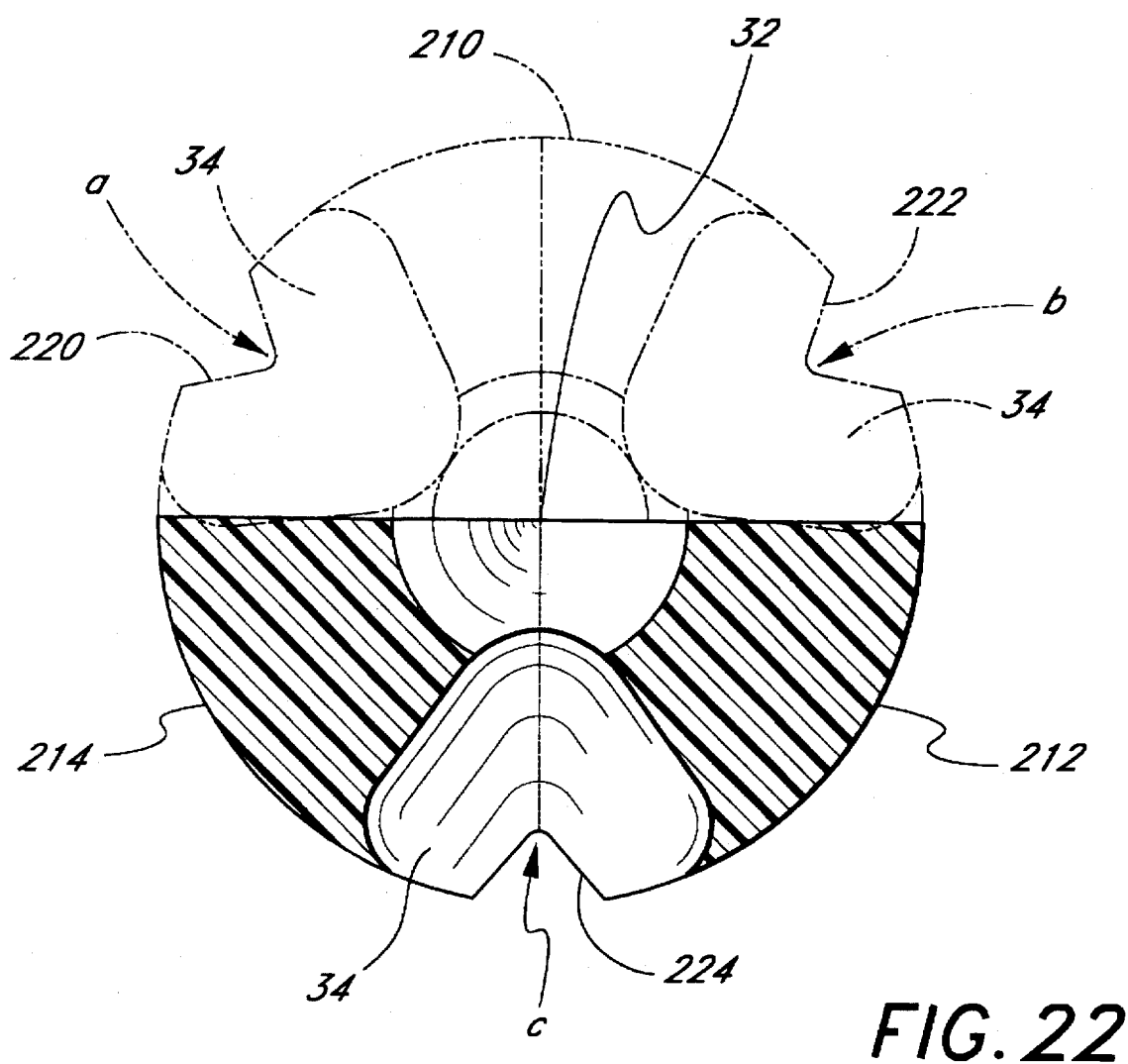
FIG. 22 is a greatly enlarged, cross-sectional view taken along line 22—22 of FIG. 14.

As best illustrated in FIG. 22, the tip 32 is designed to avoid tearing the seal. The tip 32 has three facets 210, 12, and 214 which are joined with each other along parting lines a, b, and c. This junction of the facets 210, 212, and 14 frequently is ragged and will tear the seal 36d. This is prevented by the parting lines a, b, and c, or junctions, being disposed within recesses 220, 222, and 224, respectively, to provide "buried parting lines."

Another alternative embodiment of the valve 10 using the seal 36d is shown in FIG. 8 and FIGS. 19 through 21. In this embodiment, the inner wall 160 of the upper end of the conduit 20 is provided with at least one, and preferably, a plurality of radial indentations 107. The indentations 107 are elongated and disposed generally parallel to the longitudinal axis of the valve 10 in a symmetrical, star-like configuration. Each indentation has opposed lateral edges 162 which engage the seal 36d upon compression of the seal 36d. The indentations provide space into which the seal 36d expands upon compression.

Figure 23:
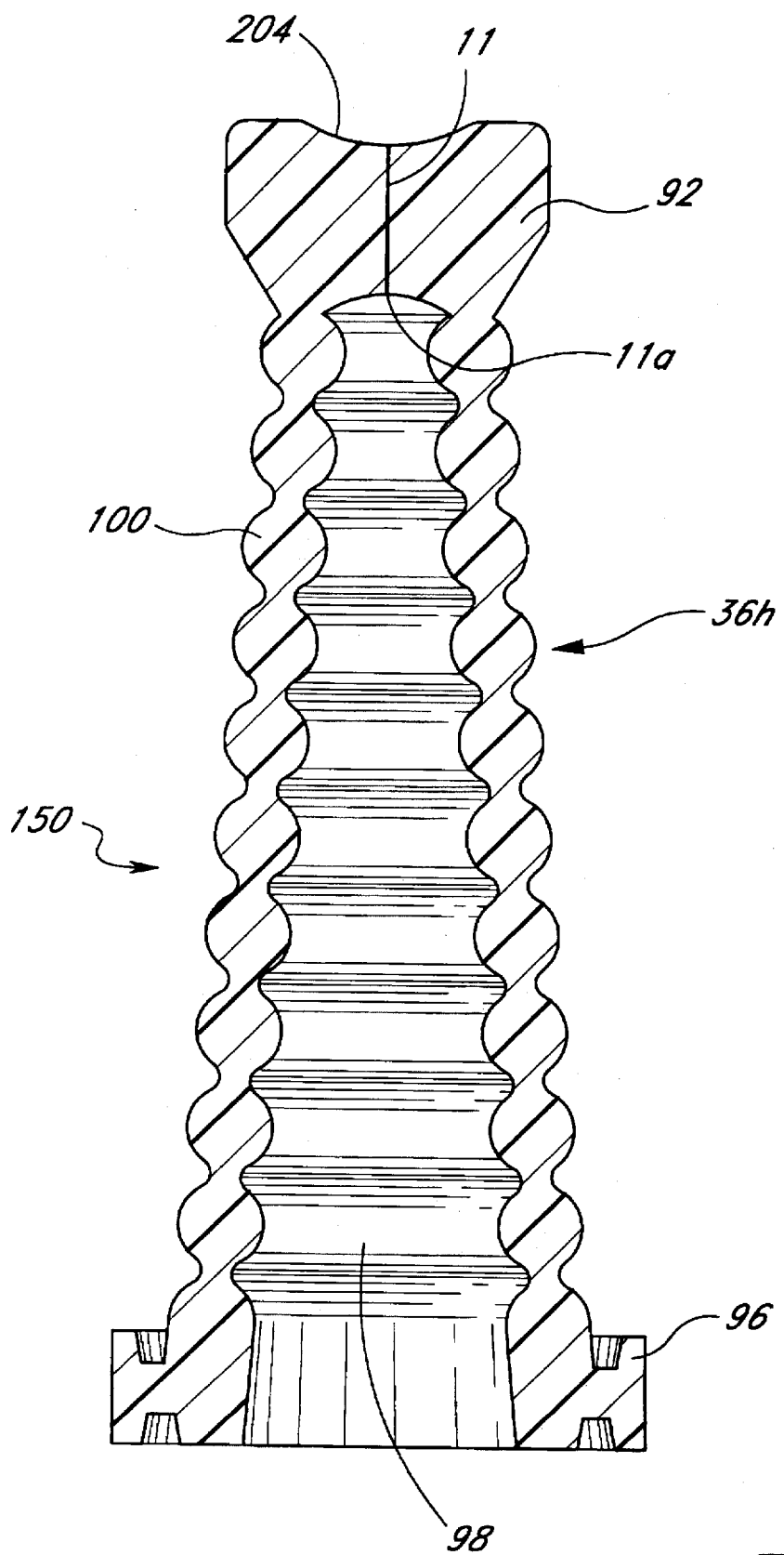
FIG. 23 is a longitudinal cross-sectional view of another preferred embodiment of the seal.

Another preferred embodiment of the seal 36h is shown in FIGS. 23 through 25 and 27. In this embodiment, the seal 36h comprises a seal cap 92 having a saucer-like depression 204 (FIG. 23). The seal 36h contains a slit 11 having a proximal end adjacent depression 204 and a distal end 11a at the distal end of seal cap 92. Referring to FIG. 23, circular tires 100 similar to those in FIG. 13 are provided. The seal 36h has an internal cavity 98. Further, the seal 36h preferably has a seal lip 96 as discussed in more detail above.

Figure 8:
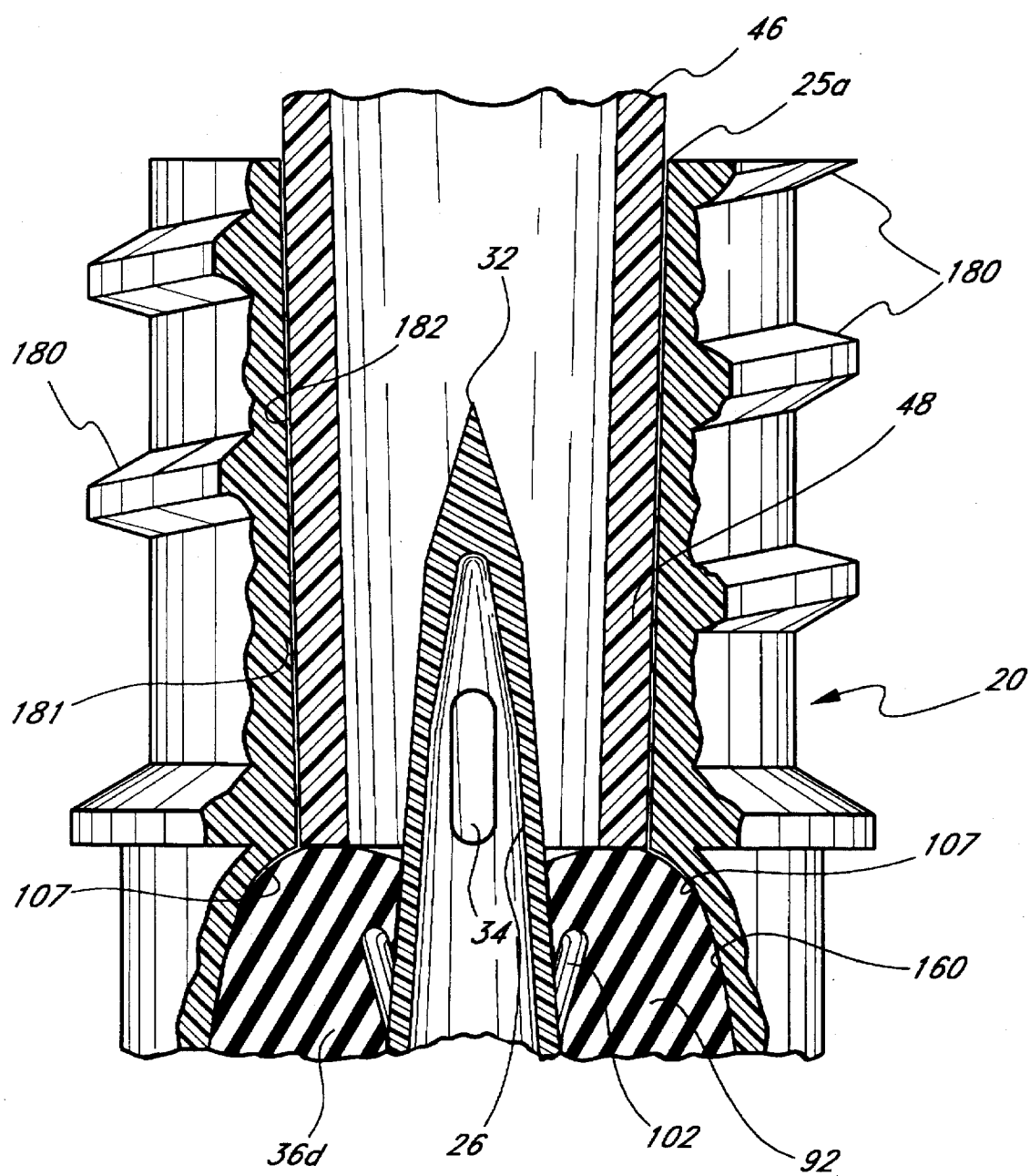
FIG. 8 is a schematic illustration of an ANSI delivery end of a medical implement compressing the seal of a valve.

As best shown in FIG. 8, the wall 181 of the proximal end of the upper conduit 20 is tapered inward at the same angle as the nose 48 of the syringe 46. In accordance with ANSI standards, the taper is 0.006 inch per linear inch. The wall 182 of the syringe nose 48 bears against the wall 181 as the nose slides into the opening 25a to push the seal 36d inward compressing it and forcing the tip 32 of the spike 36 to enter the slit 11. The seal 36d expands upon compression to fill essentially completely the upper portions of the indentations 107. Some sections of the seal 36d are wedged between the edges 162 and other sections fill the indentations 107. As the liquid flows through the nose 48 through holes 34, air in the nose 48 is forced out of the nose 48 and expelled from the valve 10 between the walls 181 and 182. Thus, essentially the entire prescribed dosage is delivered through the valve 10 to the patient. Fluid flows through the through-holes 34, but does not leak between either the seal 36d and the wall 181 or between the abutting walls 181 and 182.

FIGS. 15, 16, 17, and 18 depict embodiments of seals, namely, seal 36e, seal 36f, and seal 36g, which are substantially the same as the seals 36a (FIG. 10), seal 36b (FIG. 11), and seal 36c (FIG. 12), except the side wall 150 employing the circular tires 100 is used in place of the accordion wall portion 94.

Other components of the valve interact with the various embodiments of the seal in a similar fashion to their interaction with seal 36 of FIG. 2. Prior to use of the valve 10, it is preferable that the seal caps 40 or 92 be pierced centrally by a steel needle in the axial direction, precutting the seal to provide the slit 11 in order to allow for more rapid decompression and reformation of the seal upon piercing by the spike 26. The seals are advantageously formed from a material which can repeatedly reseal and prevent fluid from flowing around the seal material. The seal 36 should also be capable of being forced down and then spring back into position to reseal the valve. Material that is too soft will not reseal effectively; however, will not be capable of springing back after opening of the valve. Material that is too hard will provide sufficient spring force; however, will not effectively seal. Thus, in a preferred embodiment, the seal is formed from a silicone having a hardness in the range from 30–70 Shore durometer units, and more preferably in the range 40–50 Shore durometer units. A cure silicone polymer in the preferred hardness range is available from Wacker Silicone Corp. of Adrian, Mich. In some valve embodiments, it is desirable to provide additional lubricity to the seal 36 to allow it to spring back and reseal more effectively. Dow Chemical Co. produces a silicone formulation with silicone oil built in to provide this additional lubricity.

In general, the closing of the valve 10 is provided not by the side wall of the seal 36 which immediately covers the through-holes 34, but by the seal cap 40, or seal cap 92 filling the proximal end of the cavity 98 and the opening 25a. Thus, the seal caps 40 and 92 are sufficiently thick to reseal the opening 25a effectively after valve closure. However, the seal caps 40 and 92 should also be sufficiently thin to allow them to readily return to the closed position. Preferably the thickness of the caps 40 and 92 ranges between 0.075 and 0.500 inch and more preferably may be approximately 0.100 inch.

The valve can be provided in a sterile and disposable form such that after its use in a given installation is exhausted, the device is discarded. However, as described above, in any given installation, the valve can be reused multiple times. Since the valve does not employ needles, there is little chance that the device will inadvertently cause skin puncture. Therefore, the extra precautions required for handling and disposing of needles is obviated. It will be apparent from the detailed description provided herein that the valve can provide for the elimination of nearly all needles used in the medical environment. With the use of the valve described above, the need for all needles except those that are directly input into a patient is, advantageously, eliminated.

The valve 10 is used to provide a closed, patient access system for transferring a predetermined amount of medication from a remote source to the patient. The valve 10 is connected by the distal end to the patient, for example, a vein or artery in fluid communication with the valve. Blood fills the valve, but the seal 36d, for example, prevents any blood from leaking from the valve. The delivery end or nose 48 of the medical implement is inserted into the valve as depicted in FIG. 8, pushing the nose 48 against the seal to compress the seal sufficiently to allow the tip 32 of the spike 24 to pierce the seal and enter said delivery end. The predetermined amount of medication in its entirety may now be transferred through the nose 48 into the valve 10 and into the patient. Since the nose 48 and seal 36d engage in a manner so that the tip 32 of the spike element 24, upon piercing the seal, meets the seal to avoid formation of any dead space at the interface between nose 48 and the seal surface 40b. Transfer directly through the valve 10 of essentially the entire predetermined amount of medication from the syringe 46 to the patient, so that essentially none of said predetermined amount is collected in any dead space in the valve, is accomplished. Upon withdrawing the nose 48 from the valve 10 the seal 36d returns to the decompressed state to close the valve and maintain while in said decompressed state a fluid tight seal even at high pressures and after repeated uses.

Another alternative embodiment of the seal, a seal 36h, is shown in FIG. 23. In this embodiment, the seal 36h is similar to seal 36d and is comprised of a seal cap 92, seal lip 96, and a side wall 150 comprised of circular tires 100 stacked in series one on top of an adjacent larger diameter lower tire. Side wall 150 defines cavity 98. The circular tires are preferably solid throughout the diameter of the cross-section thereof. These circular tires will deform and reform upon, respectively, compression and decompression of the seal 36h, thereby exposing or covering a spike (not shown) as the case may be.

Seal 36h also has a precut slit 11 in seal cap 92 lying along the longitudinal axis of the seal 36h. Slit 11 remains sealed when seal 36h is in a decompressed state. As explained earlier, precutting the seal to provide slit 11 allows for more rapid decompression and reformation of the seal upon piercing by the spike. Unlike seal 36d, however, seal cap 92 of seal 36h is substantially solid without having any pressure responsive member as is employed in seal cap 92 for seal 36d.

Figure 24:
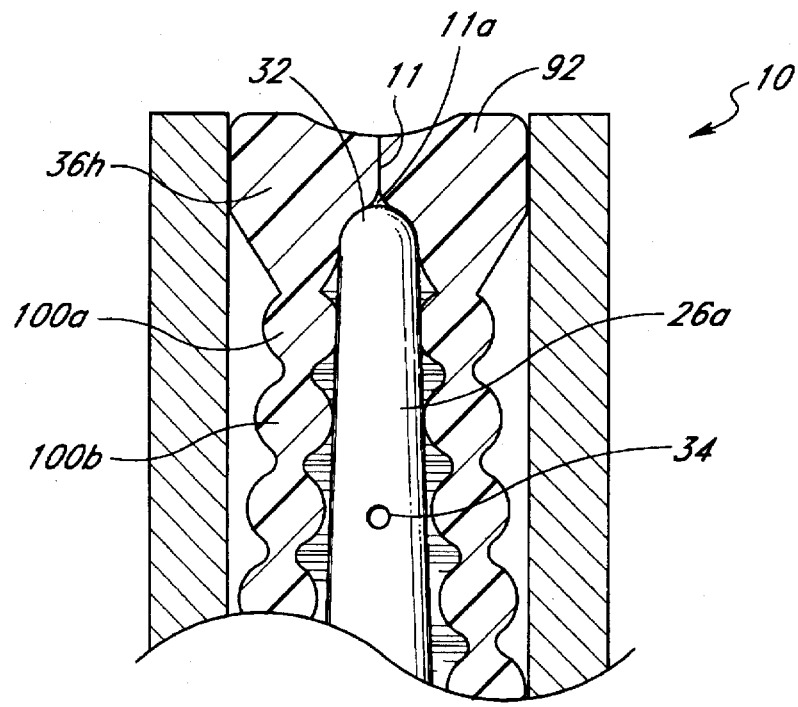
FIG. 24 is a partial cross-sectional view, after assembly, of the valve shown utilizing the seal of FIG. 23 and another preferred embodiment of the spike.

An alternative embodiment of the present invention using seal 36h is shown in FIG. 24. Spike 26a, residing within cavity 98 and having a proximal end with a tip 32 embedded in seal cap 92, is shown to be more tubular, and less frustoconical than the spike 26 illustrated in other embodiments. Furthermore, the tip 32 of spike 26a is a blunt, rounded end, unlike the pointed tip of spike 26. Because the end is rounded, the seal cap is not subjected to deterioration through tearing by spike tip 32. Thus a tear ring for the seal, as shown in FIG. 14 for example, is not necessary for this embodiment.

Another feature of this embodiment is the arrangement of the spike 26a with the seal 36h when the seal 36h is in a decompressed state. In this state, rounded tip 32 of spike 36h is positioned to be embedded in slit entryway 11a, while slit 11 remains closed to any fluid flow. FIG. 24 shows the entire rounded tip 32 in contact with the distal end of seal cap 92. Additionally, the side wall circular tire closest to the proximal end of the seal, tire 100a, contacts the side wall of spike 26a. It is desirable that at least the next immediate distal circular tire, tire 100b, also be in contact with the spike 26a proximate the through-hole 34. Having a plurality of tires in contact with spike 26a proximal through-hole 34 prevents fluid from passing from cavity 98 through the proximal end of the valve 10. Without such a design, fluid would leak through through-hole 34, thereby applying enough fluid pressure on slit 11 to force slit 11 open while the seal is still in a decompressed state. Through-hole 34 should be distal the tires 100a, 100b, which contact spike 26a, so that fluid passing through through-hole 34 will not apply pressure to slit 11, and instead will be blocked by circular tires 100a and 100b creating a seal between the spike 26a and seal 36h.

During medical applications, for example when the valve 10 is connected to a patient's artery, the patient's blood flows through the holes 34 in spike 26a, filling the area in cavity 98 distal the second tire 100b. Since the fluid residing between the first two tires, 100a and 100b, and between seal cap 92 and tire 100a constitutes a very small volume, the fluid cannot exert enough pressure against the seal cap to open slit 11. Pre-cut seal cap 92 is designed to remain closed up to fluid pressure of 20 psi. Therefore, blood pressure will not open the valve 10.

Upon connection of the distal end of valve 10 with a patient's artery, however, as the blood pushes up against seal 36h, the fluid may force seal cap 92 to move proximally, thereby also pushing the sidewall tires 100 in the proximal direction. This pressure may permit blood to flow past tires 100a and 100b to place pressure on the slit 11. However, due to increased fluid pressure, the tires immediately distal first and second tires 100a and 100b move proximally and contact the spike 26a to take the original positions of tires 100a and 100b so as to ensure that a plurality of tires are always in contact with spike 26a. Because the sidewall tires 100 of seal 36h are designed to bow outward from the proximal to the distal end, the tires immediately distal tires 100a and 100b may not be in contact with spike 26a when in their original position. However, as will be understood by those of skill in the art, if fluid flows through the spike 26a, through-hole 34 and into cavity 98 of seal 36h, forcing the seal 36h to move in a proximal direction, tires distal the first tire 100a and second tire 100b will also move in a proximal direction and contact the spike 26a proximally through-hole 34 strengthening the seal between the spike 26a and the seal 36h. That is, when fluid is not contained within the cavity 98 of the valve 10, only the first tire 100a and second tire 100b contact the spike 26a. However, once fluid is introduced into the cavity 98 of the valve 10, the seal 36h may travel in a proximal direction. If this occurs, tires directly distal second tire 100b contact seal 26a in addition to the first tire 100a and second tire 100b strengthening the seal between the seal 36h and spike 26a and preventing fluid from traveling through spike 26a, through the through-hole 34 into the cavity 98 and past the tires 100 to exert pressure on the slit 11 in the seal cap 92 of seal 36h.

Figure 25:
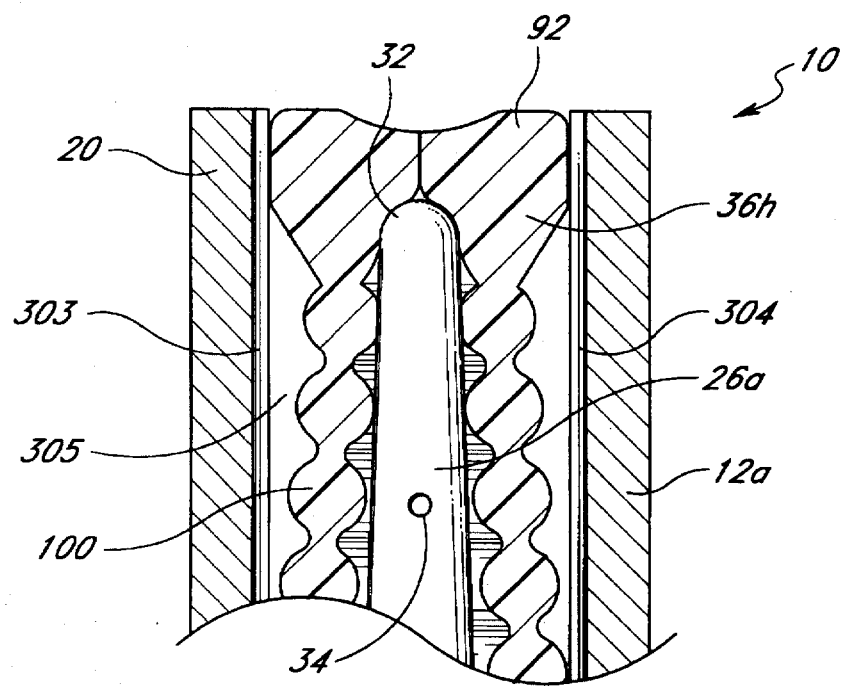
FIG. 25 is a partial cross-sectional view of the valve of FIG. 24, illustrating grooves in the housing.
Figure 28:
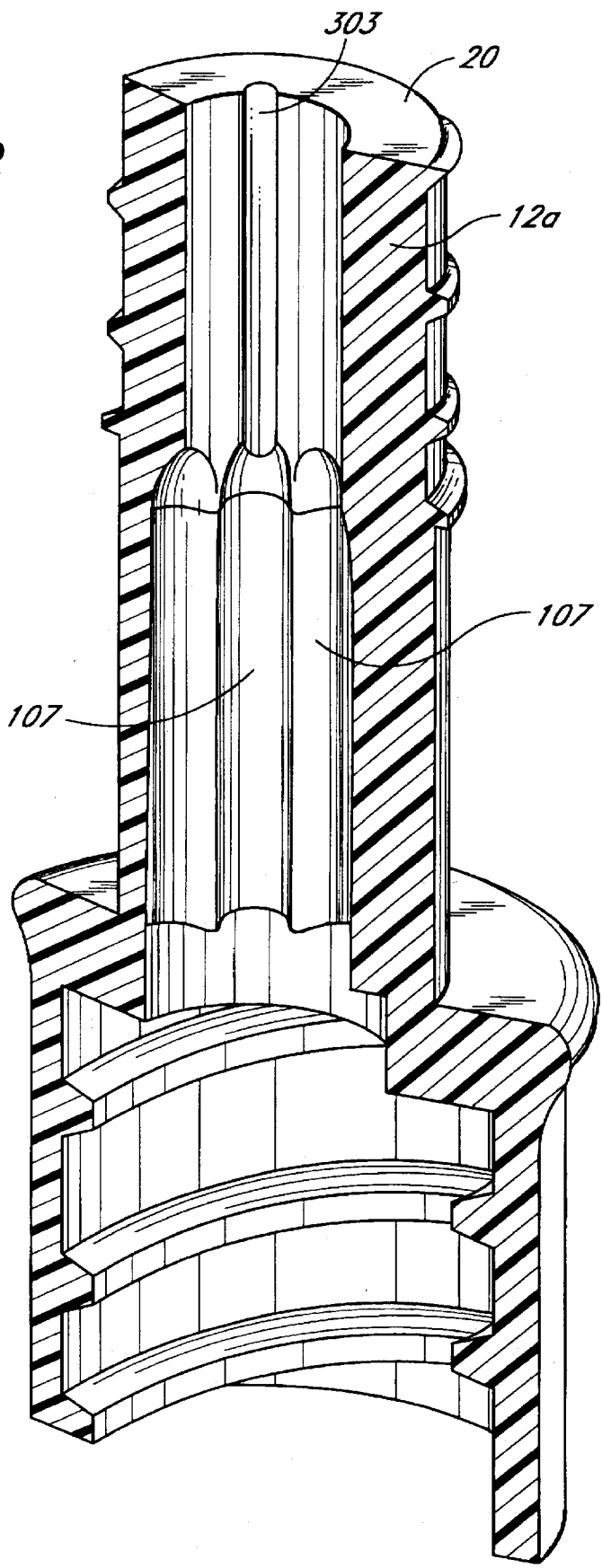
FIG. 28 is a perspective view of the housing, with sections broken away to show the wall structure of the cavity containing the seal, including the groove in the housing.

An alternative embodiment of the housing, housing 12a, is shown in FIG. 25. In this partial cross-sectional view, housing 12a is similar to housing 12, except for grooves 303, 304 that are provided along the longitudinal axis of the interior wall of the upper conduit 20. The grooves 303,304 are provided as fluid escape spaces to ensure that a perfect seal between the seal cap 92 and the inner wall 305 of the upper conduit 20 is not provided. The grooves 303, 304 preferably run from the proximal end of the upper conduit 20 distally past the portion of the upper conduit 20 in contact with the seal cap 92. As best seen in FIG. 28, the groove 303 preferably extends from the proximal end of the upper conduit 20 of the housing 12a distally to the proximal end of the radial indentations 107.

Provision of the fluid escape spaces provides the advantage of allowing any fluid residing in the space between the seal 36h and the upper conduit 20 to exit the housing upon compression of the seal 36h. Referring to FIG. 25, during routine use of the valve 10 in transferring fluid, fluid may seep into the section of the housing 12a between the seal 36h and the walls 305 of the upper conduit 20. When this area is filled with fluid and the seal cap 92 is compressed distally by a medical implement (not shown), the user may experience difficulty in forcing the seal cap 92 distally past the through-hole 34 of the spike 26a, because the sidewall tires 100 no longer have any room within the upper conduit 20 to be compressed due to the presence of the fluid. It is undesirable to require the user to apply extra force to compress the seal because oftentimes the user may twist the medical implement down onto the seal, leading to deterioration of the seal and eventual tearing. In addition, fluid between the seal 36h and the inner wall 305 of the upper conduit 20 of the housing 12a may prevent the seal 36h from compressing distal the through-hole 34 of the spike 26a. As a result, the valve 10 would not function properly.

By providing grooves 303, 304 as fluid escape spaces, fluid present between the seal 36h and the inner wall 305 of the upper conduit 20 of the housing 12a may travel proximally through the grooves 303,304 upon compression of the seal 36h by a medical implement (not shown). As the fluid is expelled from the valve 10 through the grooves 303, 304 at the proximal end of the housing 12a, the seal 36h may compress normally without use of excessive force by a user of the valve 10.

Figure 26A:
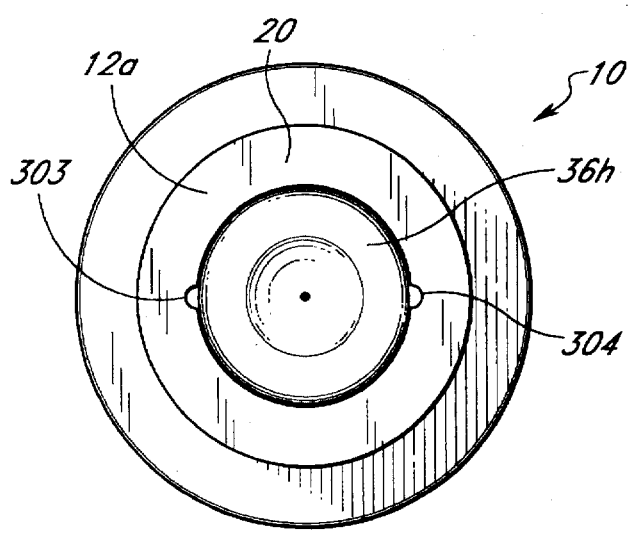
FIG. 26a is a top view of the valve of FIG. 25, illustrating the grooves in the housing.

FIG. 26a is a top plan view of the valve shown in FIG. 25. Grooves 303, 304 are shown in the upper conduit 20 of the housing 12a of the valve 10. Importantly, when the seal 36h is compressed distally by a medical implement (not shown), the seal 36h does not expand into the grooves 303, 304 thereby preventing fluid flow therethrough.

Figure 29:
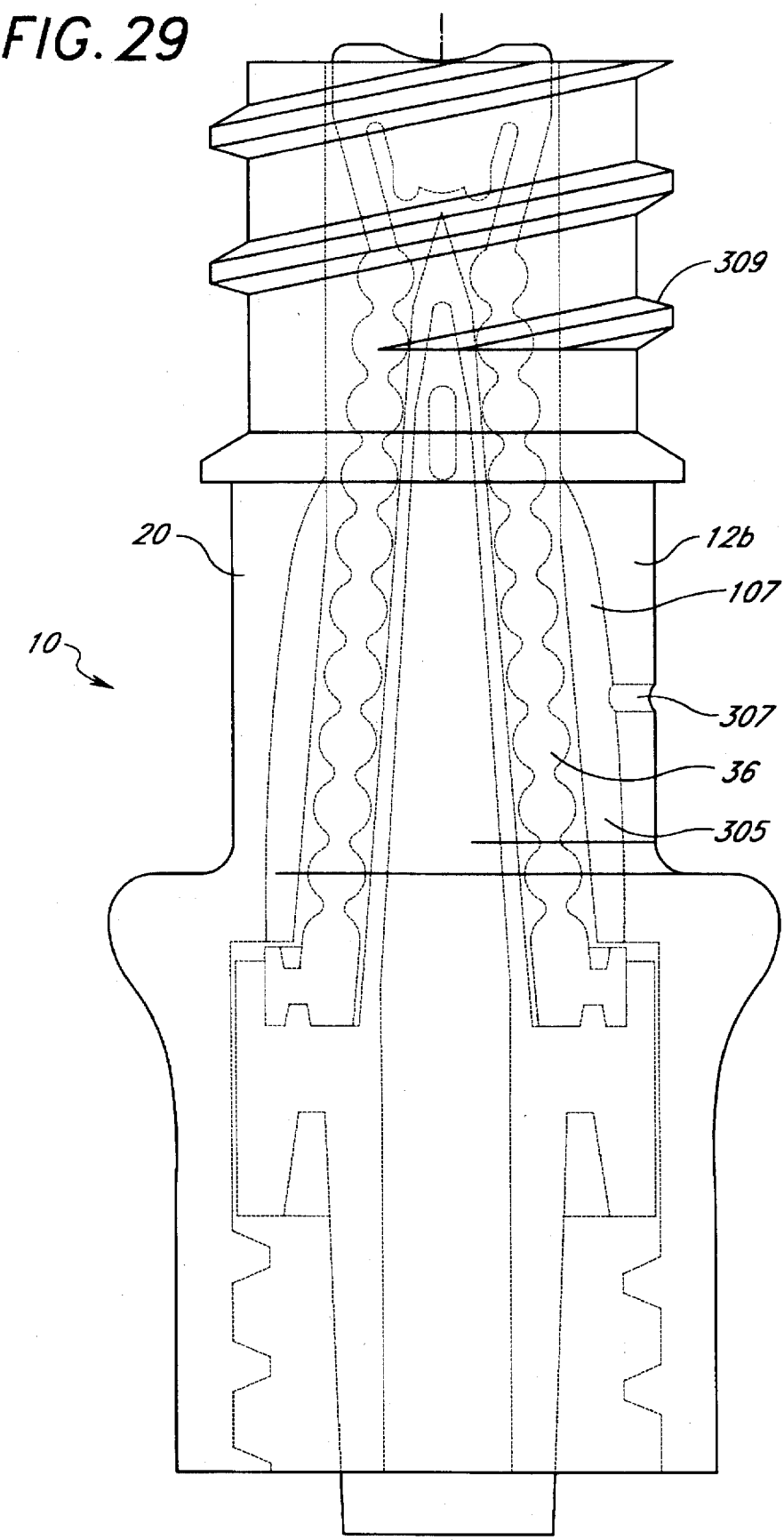
FIG. 29 is an elevational view of a preferred embodiment of the housing with a channel through the housing wall shown in phantom.

Another alternative embodiment for the housing, housing 12b, is shown in FIG. 29. The housing 12b employs a channel 307 as a fluid scape space which is substantially perpendicular to the longitudinal axis of the valve 10. A channel 307 is a bore that runs transversely through the side of the wall of the upper conduit 20, and is positioned distal to any Luer Lock threads 309 or other locking mechanism that may surround the upper conduit 20 near its proximal end. Similar to the grooves 303, 304, the channel 307 provides a passageway for fluid within the area between the seal 36 and the inner wall 305 of the upper conduit 20 to exit when the sidewall tires 100 are compressed and expand into the radial indentations 107. Since an avenue exists for the fluid to exit this area, a user does not have to apply excessive force in pushing a medical implement (not shown) distally into the valve 10.

Figure 26B:
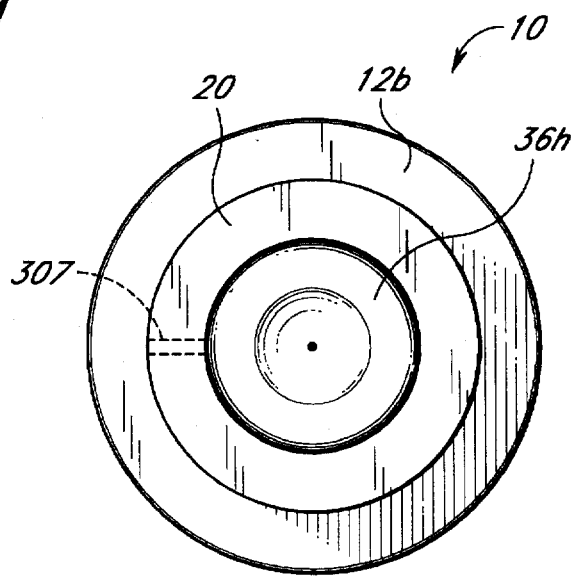
FIG. 26b is a top view of another preferred embodiment of the valve with a channel shown in phantom through the side wall of the valve.
Figure 27:
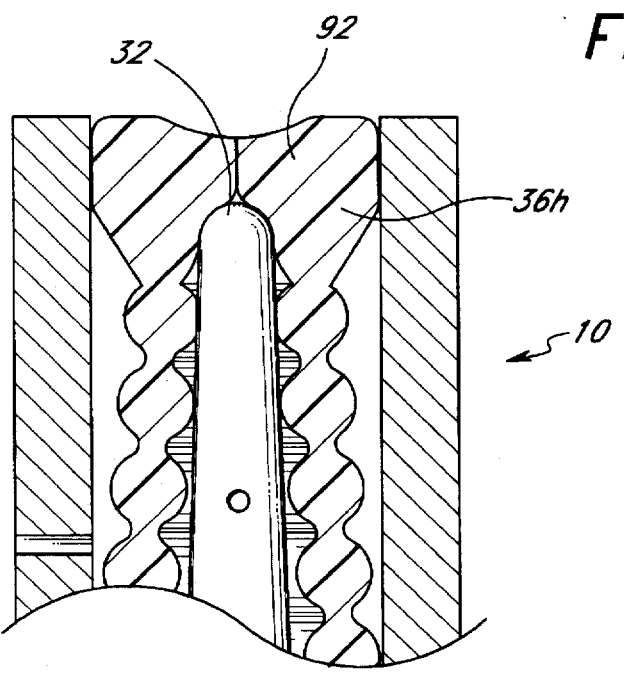
FIG. 27 is a partial cross-sectional view of the valve of FIG. 26b illustrating the channel.

FIG. 26b is a top plan view of the valve 10 shown in FIG. 29. The channel 305 is shown in phantom and is preferably located in the upper conduit 20 of the housing 12b of the valve 10. Upon compression of the seal 36h by a medical implement (not shown), fluid between the upper conduit 20 and the seal 36h is expelled from the valve 10 through the channel 307 and out the side wall of the upper conduit 20.

Thus, a channel 307 can be discharged from a groove by its injection of fluid through a side wall, rather than the proximal end of the housing 12a, as for a groove 303.

As will be easily understood by those of skill in the art, a channel and groove may be incorporated in combination to assist in expelling fluid from the valve upon compression of the seal by a medical implement. For example, upon compression of the seal, fluid could travel through a groove proximally and thereafter through a channel in communication with the groove. The channel could be located distally the proximal end of the valve. Moreover, a single groove or channel may be utilized or multiple grooves or channels may be incorporated into the valve of the present invention as will be easily understood by those of skill in the art.

Lack of a channel or groove as discussed above, may result in deterioration of the seal 36 and prevent the seal cap 92 from being pushed completely below through-hole 34. If the through-hole is not completely open, the patient will not be able to receive a constant flow rate of medication. In some situations, the delivery of an exact amount of medication at a predetermined rate may be critical for treatment, and, therefore, through-hole 34 must be completely open for passage of medication from the medical implement. The groove and/or channel ensures that the seal cap may be pushed distally the through-hole and that the seal may be compressed without any excessive force which may cause damage to the seal.

What is claimed is:

1. A medical valve comprising:
    a body including a wall structure defining an internal cavity, said body having a proximal end and a distal end, said proximal end having an opening sufficiently large to receive a tip of a delivery end of a medical implement which transfers fluid through said delivery end;
    a spike having a tip contained with said cavity, said spike having at least one hole located distal said tip, and a passageway in communication with the hole that allows fluid to flow through said spike; and
    a resilient seal in said cavity surrounding said spike, said seal having at least two tire elements along a length thereof, said seal adapted to be moved into a compressed state upon insertion of the tip of the medical implement into said opening, said seal being sufficiently resilient to return to a decompressed state upon removal of the tip of the medical implement from said opening, said seal having at least two tires in contact with said spike proximal said hole preventing flow of the fluid through said valve when said seal is in a decompressed state.

2. The valve in accordance with claim 1, wherein said fluid exerts a first, low pressure on said seal an further wherein at least one additional tire contacts said spike proximal said hole when said fluid exerts a second, higher pressure on said seal.

3. The valve in accordance with claim 1, wherein said seal extends over said tip when in its decompressed state.

4. A method of transferring a fluid through a medical valve, said valve comprising a body with an internal cavity having a proximal end and a distal end, said proximal end having an opening sufficiently large to receive a delivery end of a medical implement which transfers fluid through said delivery end, a spike within said cavity, said spike having a spike tip at the proximal end thereof and at least one hole distal said spike tip for permitting fluid to flow through said spike, and a resilient seal within said cavity of said body between said body and said spike, said seal comprising at least two tires and having at least two of said tires in contact with said spike proximal said hole to prevent flow of the fluid through said valve when said seal is in a decompressed state, said method comprising the steps of:
    (a) inserting a tip of a medical implement into said opening in the proximal end of said body;
    (b) compressing said seal in the distal direction by applying a force to the medical implement;
    (c) placing said hole and said medical implement in fluid communication'
    (d) transferring the fluid through said medical valve;
    (e) removing said medical implement from said opening in the proximal end of said body; and
    (f) permitting said tires to contact said spike proximal said hole, thereby preventing the flow of the fluid through said valve.

5. The method of claim 4, wherein step (f) is performed after step (e).

6. The method of claim 4, wherein in step (f) said fluid exerts a first, low pressure on said seal, and wherein said method additionally comprises:
    (g) said fluid exerting a second, higher pressure on said seal, wherein at least one additional tire contacts said spike proximal said hole.

7. The method of claim 4, wherein a top end of said seal extends over said tip of said spike when said seal is in a decompressed state, and wherein in said compressing step said tip of said spike is extended through said top end of said seal.

* * * * *